United States Patent
Feng et al.

(10) Patent No.: US 10,438,378 B2
(45) Date of Patent: Oct. 8, 2019

(54) SYSTEM AND METHOD FOR DETERMINING AN ACTIVITY MAP AND AN ATTENUATION MAP

(71) Applicant: UIH AMERICA, INC., Houston, TX (US)

(72) Inventors: Tao Feng, Houston, TX (US); Jizhe Wang, Houston, TX (US); Wentao Zhu, Houston, TX (US); Hongdi Li, Houston, TX (US)

(73) Assignee: UIH AMERICA, INC., Houston, TX (US)

( * ) Notice: Subject to any disclaimer, the term of this patent is extended or adjusted under 35 U.S.C. 154(b) by 96 days.

(21) Appl. No.: 15/686,157

(22) Filed: Aug. 25, 2017

(65) Prior Publication Data
US 2019/0066341 A1    Feb. 28, 2019

(51) Int. Cl.
G06T 11/00    (2006.01)
A61B 6/03    (2006.01)
G06F 17/18    (2006.01)

(52) U.S. Cl.
CPC .......... *G06T 11/003* (2013.01); *A61B 6/037* (2013.01); *G06F 17/18* (2013.01); *G06T 2207/10088* (2013.01); *G06T 2207/10104* (2013.01)

(58) Field of Classification Search
CPC ......... G06T 11/003; G06T 2207/10104; G06T 2207/10088; G06F 17/18; A61B 6/037
See application file for complete search history.

(56) References Cited

U.S. PATENT DOCUMENTS

| | | | |
|---|---|---|---|
| 8,913,810 B2 | 12/2014 | Panin et al. | |
| 9,474,495 B2 | 10/2016 | Ahn et al. | |
| 9,706,972 B1* | 7/2017 | Ahn | G06T 11/006 |
| 2013/0028496 A1* | 1/2013 | Panin | G06T 11/006 |
| | | | 382/131 |
| 2014/0177785 A1* | 6/2014 | Funk | A61B 6/032 |
| | | | 378/9 |
| 2015/0098640 A1 | 4/2015 | Berker et al. | |
| 2016/0327622 A1 | 11/2016 | Ahn et al. | |

FOREIGN PATENT DOCUMENTS

WO    WO2016197127 A1    12/2016

OTHER PUBLICATIONS

Defrise Miche et al., Time-of-flight PET data determine the attenuation sinogram up to a constant, Physics in Medicine & Biology, 2012, 18 pages.
Abolfazl Mehranian et al., MR constrained simultaneous reconstruction of activity and attenuation maps in brain TOF-PET/MR imaging, E JNMMI physics, 2014, 1 page.

* cited by examiner

*Primary Examiner* — Qian Yang
(74) *Attorney, Agent, or Firm* — Metis IP LLC

(57) ABSTRACT

The present disclosure relates to systems and methods for determining a target activity map and a target attenuation map for producing a PET image. The systems may execute the methods to acquire, based on a PET system, a first dataset relating to coincidence events with TOF information, and a second dataset relating to single events. The systems may also execute the methods to determine a target activity map and a target attenuation map based on the first dataset and the second dataset through a plurality of iterations. The systems may further execute the methods to generate the PET image based on the target activity map and the target attenuation map.

20 Claims, 10 Drawing Sheets

SYSTEM AND METHOD FOR DETERMINING AN ACTIVITY MAP AND AN ATTENUATION MAP

TECHNICAL FIELD

The present disclosure generally relates to image reconstruction, and more particularly, a system and method for determining an activity map and an attenuation map based on positron emission tomography image data.

BACKGROUND

In positron emission tomography (PET) imaging, a quantitative reconstruction of a tracer distribution requires attenuation correction. An attenuation map may be needed for attenuation correction. The attenuation map is typically acquired through a transmission scan using a computed tomography (CT) scanner or derived from magnetic resonance (MR) imaging. An attenuation map derived from MR is problematic in terms of accuracy. To provide an attenuation map from CT, a measured object may need to be exposed to a radiation dose. In another way, an attenuation map be acquired based on PET data and time-of-flight (TOF) information, but the quality and/or spatial resolution of the attenuation map is relatively poor. Therefore, it would be desirable to provide effective mechanisms for generating an attenuation map to correct activity distribution.

SUMMARY

A first aspect of the present disclosure relates to a system including at least one storage medium including a set of instructions for reconstructing an activity map and an attenuation map to produce a positron emission tomography (PET) image and at least one processor configured to communicate with the at least one storage medium. When executing the set of instructions, the system may be directed to acquire, based on a PET system, a first dataset relating to coincidence events with time of flight (TOF) information, and a second dataset relating to single events or delay events. The system may be directed to perform a plurality of iterations, and in each one of the plurality of iterations, the system may be directed to generate, based on the first dataset, an estimated activity map and an estimated attenuation map according to at least one image reconstruction algorithm; determine an estimated second dataset based on the estimated activity map and the estimated attenuation map; and update, based on the second dataset and the estimated second dataset, the estimated activity map and the estimated attenuation map to obtain an updated activity map and an updated attenuation map. The system may be further directed to determine a target activity map and a target attenuation map.

In some embodiments, the system may be further directed to determine, based on the first dataset, a plurality of data points associated with a boundary of a subject; and obtain an initial activity map and an initial attenuation map according to the boundary.

In some embodiments, to generate an estimated activity map and an estimated attenuation map according to at least one image reconstruction algorithm, the system may be further directed to update, according to a first algorithm, the initial activity map or the updated activity map obtained in the previous iteration to generate the estimated activity map; and update, according to a second algorithm, the initial attenuation map or the updated attenuation map obtained in the previous iteration to generate the estimated attenuation map.

In some embodiments, the first algorithm may be a maximum likelihood expectation maximization (MLEM) algorithm and the second algorithm may be a maximum likelihood for transmission tomography (MLTR) algorithm.

In some embodiments, the system may be further directed to obtain, based on the first dataset, a third dataset relating to coincidence events without TOF information; and determine a plurality of pixel values corresponding to the image domain of the third dataset.

In some embodiments, to update the estimated activity map and the estimated attenuation map, the system may be further directed to determine a first relationship associated with the estimated activity map, the second dataset, and the estimated second dataset; and determine a second relationship associated with the estimated attenuation map, the second dataset, the estimated second dataset, and the plurality of pixel values.

In some embodiments, to update the estimated activity map and the estimated attenuation map, the system may be further directed to update the estimated activity map to obtain the updated activity map according to the first relationship; and update the estimated attenuation map to obtain the updated attenuation map according to the second relationship.

In some embodiments, at least one of the first relationship and the second relationship may include a ratio of the second dataset to the estimated second dataset.

In some embodiments, the target activity map and the target attenuation map may be determined when at least one of the estimated activity map, the estimated attenuation map, the updated activity map and the updated attenuation map is convergent, or an iteration count of the plurality of iterations exceeds a predetermined threshold.

In some embodiments, the system may be further directed to generate, based on the target activity map and the target attenuation map, the PET image.

A second aspect of the present disclosure relates to a method for reconstructing an activity map and an attenuation map to produce a positron emission tomography (PET) image. The method may include acquiring, based on a PET system, a first dataset relating to coincidence events with time of flight (TOF) information, and a second dataset relating to single events or delay events. The method may further include performing a plurality of iterations, and in each one of the plurality of iterations, the method comprising generating, based on the first dataset, an estimated activity map and an estimated attenuation map according to at least one image reconstruction algorithm; determining an estimated second dataset based on the estimated activity map and the estimated attenuation map; and updating, based on the second dataset and the estimated second dataset, the estimated activity map and the estimated attenuation map to obtain an updated activity map and an updated attenuation map. The method may further include determining a target activity map and a target attenuation map.

In some embodiments, the generating an estimated activity map and an estimated attenuation map according to at least one image reconstruction algorithm may further include updating, according to a first algorithm, an initial activity map or the updated activity map obtained in the previous iteration to generate the estimated activity map; and updating, according to a second algorithm, an initial attenuation map or the updated attenuation map obtained in the previous iteration to generate the estimated attenuation map.

In some embodiments, the first algorithm may be a maximum likelihood expectation maximization (MLEM) algorithm and the second algorithm may be a maximum likelihood for transmission tomography (MLTR) algorithm.

In some embodiments, the updating the estimated activity map and the estimated attenuation map further include updating the estimated activity map to obtain the updated activity map according to a first relationship; and updating the estimated attenuation map to obtain the updated attenuation map according to a second relationship.

In some embodiments, at least one of the first relationship and the second relationship may include a ratio of the second dataset to the estimated second dataset.

In some embodiments, the target activity map and the target attenuation map may be determined when at least one of the estimated activity map, the estimated attenuation map, the updated activity map and the updated attenuation map is convergent, or an iteration count of the plurality of iterations exceeds a predetermined threshold.

In some embodiments, the method may further include generating, based on the target activity map and the target attenuation map, the PET image.

A third aspect of the present disclosure relates to a method for processing, by a processor of a computer, positron emission tomography (PET) information obtained from a PET detector, the method may include acquiring positron emission tomography (PET) data generated by scanning a subject. The method may also include acquiring single events or delay events based on the PET data. The method may also include performing following steps to obtain a target activity map and a target attenuation map. The steps may include i) iteratively reconstructing an estimated activity map and an estimated attenuation map based on the PET data; ii) determining estimated single events or estimated delay events based on the estimated activity map and the estimated attenuation map; iii) updating the estimated activity map and the estimated attenuation map based on the estimated single events and the scanned single events, or the estimated delay events and the scanned delay events to generate an updated activity map and an updated attenuation map; and iv) repeating i) through iii), until one or more termination criteria are satisfied.

In some embodiments, the termination criteria are at least one of the estimated activity map, the estimated attenuation map, the updated activity map and the updated attenuation map is convergent, or an iteration count of the plurality of iterations exceeds a predetermined threshold.

A fourth aspect of the present disclosure relates to a system having at least one processor and storage. The system may include an acquisition module configured to acquire, based on a PET system, a first dataset relating to coincidence events with time of flight (TOF) information, and a second dataset relating to single events or delay events. The system may further include a reconstruction module configured to perform a plurality of iterations, and in each one of the plurality of iterations, the reconstruction module may be configured to generate, based on the first dataset, an estimated activity map and an estimated attenuation map according to at least one image reconstruction algorithm; determine an estimated second dataset based on the estimated activity map and the estimated attenuation map; and update, based on the second dataset and the estimated second dataset, the estimated activity map and the estimated attenuation map to obtain an updated activity map and an updated attenuation map. The reconstruction module may be further configured to determine a target activity map and a target attenuation map.

In some embodiments, the reconstruction module may further include a data updating unit configured to obtain, based on the first dataset, a third dataset relating to coincidence events without TOF information; and determine a plurality of pixel values corresponding to the image domain of the third dataset.

In some embodiments, the data updating unit may be further configured to determine a first relationship associated with the estimated activity map, the second dataset, and the estimated second dataset; and determine a second relationship associated with the estimated attenuation map, the second dataset, the estimated second dataset, and the plurality of pixel values.

In some embodiments, the data updating unit may be further configured to update the estimated activity map to obtain the updated activity map according to the first relationship; and update the estimated attenuation map to obtain the updated attenuation map according to the second relationship.

In some embodiments, the system may further include a correction module configured to correct the target activity map by the target attenuation map to generate a PET image.

A fifth aspect of the present disclosure relates to a non-transitory computer readable medium embodying a computer program product. The computer program product may comprise instructions configured to cause a computing device to acquire, based on a PET system, a first dataset relating to coincidence events with time of flight (TOF) information, and a second dataset relating to single events or delay events. The computing device may further be caused to perform a plurality of iterations, and in each one of the plurality of iterations, the computing device may generate, based on the first dataset, an estimated activity map and an estimated attenuation map according to at least one image reconstruction algorithm; determine an estimated second dataset based on the estimated activity map and the estimated attenuation map; and update, based on the second dataset and the estimated second dataset, the estimated activity map and the estimated attenuation map to obtain an updated activity map and an updated attenuation map. The reconstruction module may be further configured to determine a target activity map and a target attenuation map.

Additional features will be set forth in part in the description which follows, and in part will become apparent to those skilled in the art upon examination of the following and the accompanying drawings or may be learned by production or operation of the examples. The features of the present disclosure may be realized and attained by practice or use of various aspects of the methodologies, instrumentalities and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. These embodiments are non-limiting exemplary embodiments, in which like reference numerals represent similar structures throughout the several views of the drawings, and wherein.

DETAILED DESCRIPTION

In the following detailed description, numerous specific details are set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments will be readily apparent to those skilled in the art, and the general principles defined herein may be applied to other embodiments and applications without departing from the spirit and scope of the present disclosure. Thus, the present disclosure is not limited to the embodiments shown, but to be accorded the widest scope consistent with the claims.

The terminology used herein is for the purpose of describing particular example embodiments only and is not intended to be limiting. As used herein, the singular forms "a," "an," and "the" may be intended to include the plural forms as well, unless the context clearly indicates otherwise. It will be further understood that the terms "comprise," "comprises," and/or "comprising," "include," "includes," and/or "including," when used in this specification, specify the presence of stated features, integers, steps, operations, elements, and/or components, but do not preclude the presence or addition of one or more other features, integers, steps, operations, elements, components, and/or groups thereof.

It will be understood that the terms "system," "engine," "unit," "module," and/or "block" used herein are one method to distinguish different components, elements, parts, sections or assembly of different levels in ascending order. However, the terms may be displaced by other expression if they achieve the same purpose.

Figure 2:
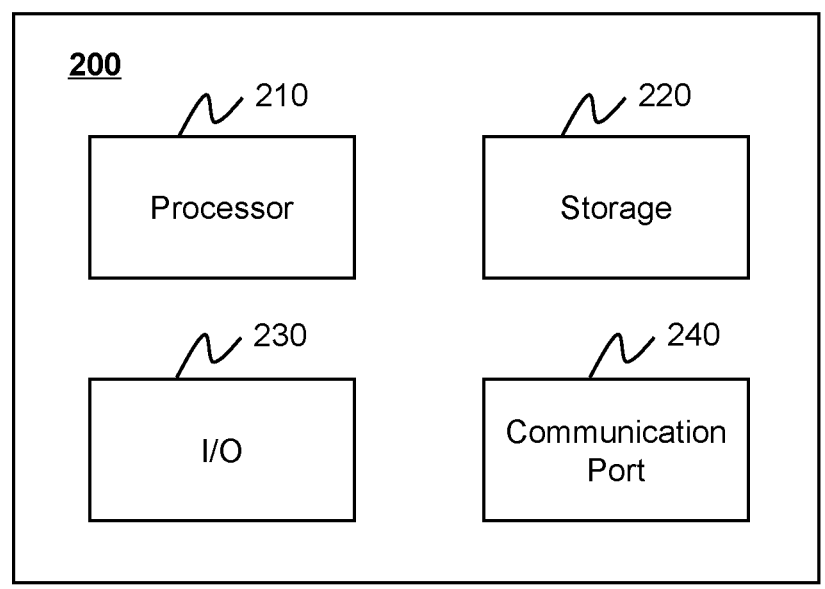
FIG. 2 is a schematic diagram illustrating exemplary hardware and/or software components of an exemplary computing device on which the processing engine may be implemented according to some embodiments of the present disclosure.

Generally, the word "module," "unit," or "block," as used herein, refers to logic embodied in hardware or firmware, or to a collection of software instructions. A module, a unit, or a block described herein may be implemented as software and/or hardware and may be stored in any type of non-transitory computer-readable medium or other storage device. In some embodiments, a software module/unit/block may be compiled and linked into an executable program. It will be appreciated that software modules can be callable from other modules/units/blocks or from themselves, and/or may be invoked in response to detected events or interrupts. Software modules/units/blocks configured for execution on computing devices (e.g., processor 210 as illustrated in FIG. 2) may be provided on a computer-readable medium, such as a compact disc, a digital video disc, a flash drive, a magnetic disc, or any other tangible medium, or as a digital download (and can be originally stored in a compressed or installable format that needs installation, decompression, or decryption prior to execution). Such software code may be stored, partially or fully, on a storage device of the executing computing device, for execution by the computing device. Software instructions may be embedded in a firmware, such as an EPROM. It will be further appreciated that hardware modules/units/blocks may be included in connected logic components, such as gates and flip-flops, and/or can be included of programmable units, such as programmable gate arrays or processors. The modules/units/blocks or computing device functionality described herein may be implemented as software modules/units/blocks, but may be represented in hardware or firmware. In general, the modules/units/blocks described herein refer to logical modules/units/blocks that may be combined with other modules/units/blocks or divided into sub-modules/sub-units/sub-blocks despite their physical organization or storage. The description may be applicable to a system, an engine, or a portion thereof.

It will be understood that when a unit, engine, module or block is referred to as being "on," "connected to," or "coupled to," another unit, engine, module, or block, it may be directly on, connected or coupled to, or communicate with the other unit, engine, module, or block, or an intervening unit, engine, module, or block may be present, unless the context clearly indicates otherwise. As used herein, the term "and/or" includes any and all combinations of one or more of the associated listed items.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings are for the purpose of illustration and description only and are not intended to limit the scope of the present disclosure. It is understood that the drawings are not to scale.

For illustration purposes, the following description is provided to help better understanding an imaging process. It is understood that this is not intended to limit the scope of the present disclosure. For persons having ordinary skills in the art, a certain amount of variations, changes and/or modifications may be deducted under guidance of the present disclosure. Those variations, changes and/or modifications do not depart from the scope of the present disclosure.

The present disclosure relates to systems and methods for determining a target activity map and a target attenuation map. The systems and methods may acquire, based on a PET system, a first dataset relating to coincidence events with time of flight (TOF) information, and a second dataset relating to single events or delay events. The systems and methods may further perform a plurality of iterations, and in each one of the plurality of iterations, the systems and methods may generate, based on the first dataset, an estimated activity map and an estimated attenuation map according to at least one image reconstruction algorithm; determine an estimated second dataset based on the estimated activity map and the estimated attenuation map; and update, based on the second dataset and the estimated second dataset, the estimated activity map and the estimated attenuation map to obtain an updated activity map and an updated attenuation map. The systems and the methods may further determine a target activity map and a target attenuation map. The systems and methods according to some embodiments of the present disclosure may determine an activity map and attenuation map by combining single events and/or delay events and coincidence events with TOF information.

Figure 1:
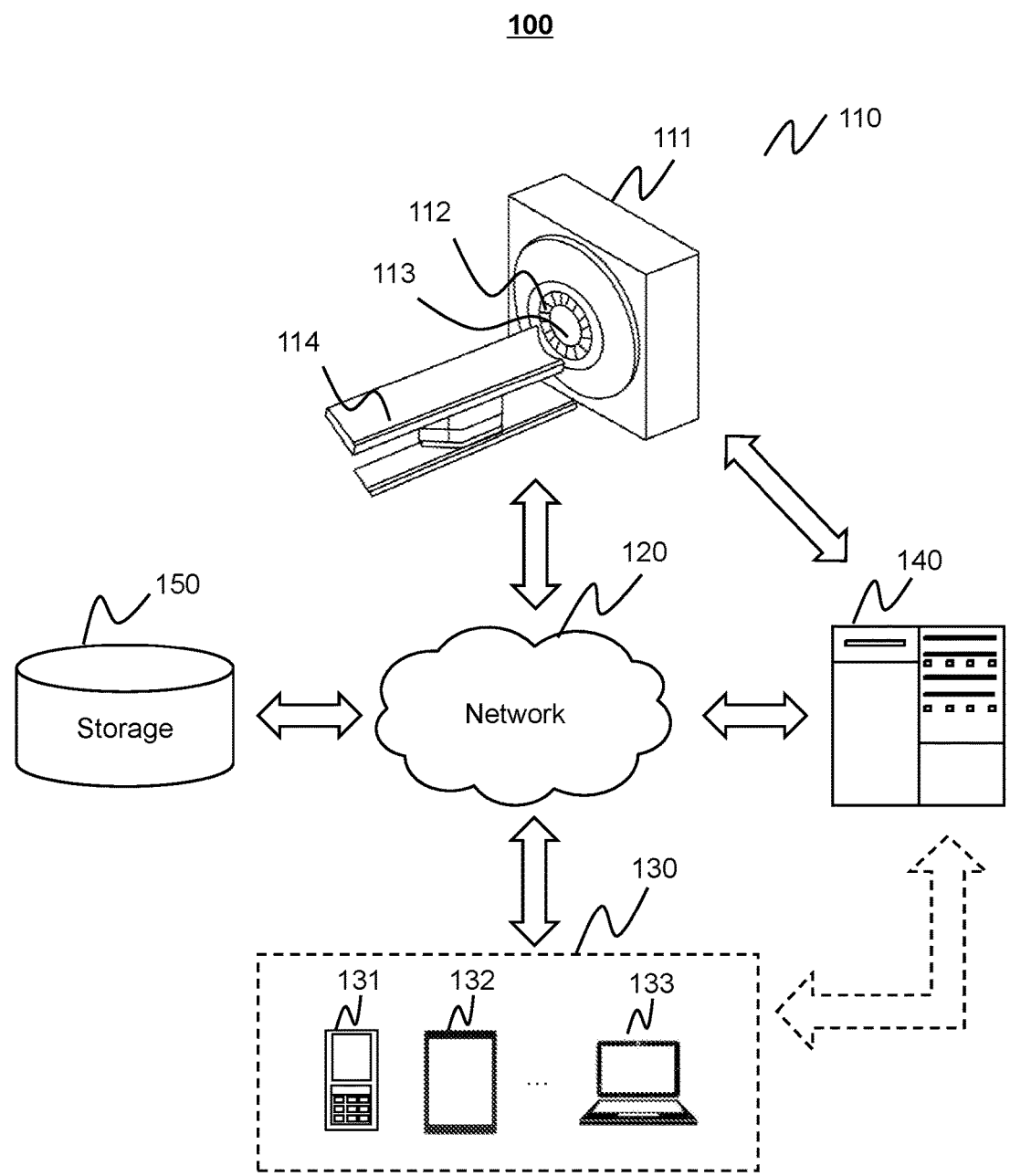
FIG. 1 is a schematic diagrams illustrating an exemplary imaging system 100 according to some embodiments of the present disclosure.

FIG. 1 is a schematic diagram illustrating an exemplary imaging system 100 according to some embodiments of the present disclosure. As shown, the imaging system 100 may include a scanner 110, a network 120, one or more terminals 130, a processing engine 140, and a storage 150. In some embodiments, the scanner 110, the processing engine 140, the storage 150, and/or the terminal(s) 130 may be connected to and/or communicate with each other via a wireless connection (e.g., the network 120), a wired connection, or a combination thereof. The connection between the components in the imaging system 100 may be variable. Merely by way of example, the scanner 110 may be connected to the processing engine 140 through the network 120, as illustrated in FIG. 1. As another example, the scanner 110 may be connected to the processing engine 140 directly. As a further example, the storage 150 may be connected to the processing engine 140 through the network 120, as illustrated in FIG. 1, or connected to the processing engine 140 directly.

The scanner 110 may scan an object, and/or generate a plurality of data relating to the object. In some embodiments, the scanner 110 may be a medical imaging device, for example, a PET device, a PET-CT device, a PET-MRI device, etc. The scanner 110 may include a gantry 111, a detector 112, a detection region 113, and a table 114. A subject may be placed on the table 114 for scanning. In the present disclosure, "object" and "subject" are used interchangeably. The detector 112 may detect radiation events (e.g., gamma photons) emitted from the detection region 113. In some embodiments, the detector 112 may include one or more detector units. The detector units may be implemented in any suitable manner, for example, a ring, an arc, a rectangle, an array, or the like, or any combination thereof. In some embodiments, a detector unit may include one or more crystal elements (e.g., scintillators) and/or one or more photomultipliers (e.g., silicon photomultiplier (SiPM), photomultiplier tube (PMT)). The table 114 may position a subject in the detection region 113. In some embodiments, the detected radiation events may be stored or archived in a storage (e.g., the storage 150), displayed on a display, or transferred to an external storage device via a cable, or a wired or wireless network (e.g., the network 120). In some embodiments, a user may control the scanner 110 via the processing engine 140.

In some embodiments, before scanning, a radioactive tracer isotope may be injected into the subject to be scanned. One or more atoms of the tracer isotope may be chemically incorporated into one or more biologically active molecules in the subject. The active molecules may become concentrated in one or more tissues of interest within the subject. The tracer isotope may undergo positron emission decay and emit one or more positrons. A positron may travel a short distance (e.g., about 1 mm) within a tissue of interest, lose kinetic energy and interact with an electron of the subject. The positron and the electron may annihilate and produce a pair of annihilation photons. The pair of annihilation photons (or radiation rays) may move in approximately opposite directions. A plurality of radiation rays may reach the detector 112 and be detected by the detector 112.

In some embodiments, one or more coincidence events may be determined based on the interaction positions and the interaction times of a plurality of received radiation rays. If two radiation rays are received and interact with two scintillators within a certain time window (e.g., 1 nanosecond, 2 nanoseconds, 5 nanoseconds, 10 nanoseconds, 20 nanoseconds, etc.), the two radiation rays may be determined to come from the same annihilation, and regarded as a coincidence event. The coincidence event may be assigned to a line of response (LOR) joining the two relevant scintillators that detect the coincidence event. The coincidence events that are assigned to the same line of response (LOR) may be projected and image data may be generated.

The network 120 may include any suitable network that can facilitate exchange of information and/or data for the imaging system 100. In some embodiments, one or more components of the imaging system 100 (e.g., the scanner 110, the terminal 130, the processing engine 140, the storage 150, etc.) may communicate information and/or data with one or more other components of the imaging system 100 via the network 120. For example, the processing engine 140 may obtain image data from the scanner 110 via the network 120. As another example, the processing engine 140 may obtain user instructions from the terminal(s) 130 via the network 120. The network 120 may include a public network (e.g., the Internet), a private network (e.g., a local area network (LAN), a wide area network (WAN)), etc.), a wired network (e.g., an Ethernet network), a wireless network (e.g., an 802.11 network, a Wi-Fi network, etc.), a cellular network (e.g., a Long Term Evolution (LTE) network), a frame relay network, a virtual private network ("VPN"), a satellite network, a telephone network, routers, hubs, switches, server computers, and/or any combination thereof. Merely by way of example, the network 120 may include a cable network, a wireline network, a fiber-optic network, a telecommunications network, an intranet, a wireless local area network (WLAN), a metropolitan area network (MAN), a public telephone switched network (PSTN), a Bluetooth™ network, a ZigBee™ network, a near field communication (NFC) network, or the like, or any combination thereof. In some embodiments, the network 120 may include one or more network access points. For example, the network 120 may include wired and/or wireless network access points such as base stations and/or internet exchange points through which one or more components of the imaging system 100 may be connected to the network 120 to exchange data and/or information.

The terminal(s) 130 may include a mobile device 131, a tablet computer 132, a laptop computer 133, or the like, or any combination thereof. In some embodiments, the mobile device 131 may include a smart home device, a wearable device, a mobile device, a virtual reality device, an augmented reality device, or the like, or any combination thereof. In some embodiments, the smart home device may include a smart lighting device, a control device of an intelligent electrical apparatus, a smart monitoring device, a smart television, a smart video camera, an interphone, or the like, or any combination thereof. In some embodiments, the wearable device may include a bracelet, a footgear, eyeglasses, a helmet, a watch, clothing, a backpack, a smart accessory, or the like, or any combination thereof. In some embodiments, the mobile device may include a mobile phone, a personal digital assistance (PDA), a gaming device, a navigation device, a point of sale (POS) device, a laptop, a tablet computer, a desktop, or the like, or any combination thereof. In some embodiments, the virtual reality device and/or the augmented reality device may include a virtual reality helmet, virtual reality glasses, a virtual reality patch, an augmented reality helmet, augmented reality glasses, an augmented reality patch, or the like, or any combination thereof. For example, the virtual reality device and/or the augmented reality device may include a Google Glass™, an Oculus Rift™, a Hololens™, a Gear VR™, etc. In some embodiments, the terminal(s) 130 may be part of the processing engine 140.

The processing engine 140 may process data and/or information obtained from the scanner 110, the terminal(s) 130, and/or the storage 150. For example, the processing engine 140 may process image data and reconstruct an image based on the image data. In some embodiments, the processing engine 140 may be a single server or a server group. The server group may be centralized or distributed. In some embodiments, the processing engine 140 may be local or remote. For example, the processing engine 140 may access information and/or data stored in the scanner 110, the terminal(s) 130, and/or the storage 150 via the network 120. As another example, the processing engine 140 may be directly connected to the scanner 110, the terminal(s) 130, and/or the storage 150 to access stored information and/or data. In some embodiments, the processing engine 140 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof. In some embodiments, the processing engine 140 may be implemented by a computing device 200 having one or more components as illustrated in FIG. 2. In some embodiments, the processing engine 140, or a portion of the processing engine 140 may be integrated into the scanner 110.

The storage 150 may store data, instructions, and/or any other information. In some embodiments, the storage 150 may store data obtained from the terminal(s) 130 and/or the processing engine 140. In some embodiments, the storage 150 may store data and/or instructions that the processing engine 140 may execute or use to perform exemplary methods described in the present disclosure. In some embodiments, the storage 150 may include a mass storage, a removable storage, a volatile read-and-write memory, a read-only memory (ROM), or the like, or any combination thereof. Exemplary mass storage may include a magnetic disk, an optical disk, a solid-state drive, etc. Exemplary removable storage may include a flash drive, a floppy disk, an optical disk, a memory card, a zip disk, a magnetic tape, etc. Exemplary volatile read-and-write memory may include a random access memory (RAM). Exemplary RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. Exemplary ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 150 may be implemented on a cloud platform. Merely by way of example, the cloud platform may include a private cloud, a public cloud, a hybrid cloud, a community cloud, a distributed cloud, an inter-cloud, a multi-cloud, or the like, or any combination thereof.

In some embodiments, the storage 150 may be connected to the network 120 to communicate with one or more other components in the imaging system 100 (e.g., the processing engine 140, the terminal(s) 130, etc.). One or more components in the imaging system 100 may access the data or instructions stored in the storage 150 via the network 120. In some embodiments, the storage 150 may be directly connected to or communicate with one or more other components in the imaging system 100 (e.g., the processing engine 140, the terminal(s) 130, etc.). In some embodiments, the storage 150 may be part of the processing engine 140.

FIG. 2 is a schematic diagram illustrating exemplary hardware and/or software components of an exemplary computing device 200 on which the processing engine 120 may be implemented according to some embodiments of the present disclosure. As illustrated in FIG. 2, the computing device 200 may include a processor 210, a storage 220, an input/output (I/O) 230, and a communication port 240.

The processor 210 may execute computer instructions (e.g., program code) and perform functions of the processing engine 120 in accordance with techniques described herein. The computer instructions may include, for example, routines, programs, objects, components, data structures, procedures, modules, and functions, which perform particular functions described herein. For example, the processor 210 may process image data obtained from the scanner 110, the terminal(s) 130, the storage 150, and/or any other component of the imaging system 100. In some embodiments, the processor 210 may include one or more hardware processors, such as a microcontroller, a microprocessor, a reduced instruction set computer (RISC), an application specific integrated circuits (ASICs), an application-specific instruction-set processor (ASIP), a central processing unit (CPU), a graphics processing unit (GPU), a physics processing unit (PPU), a microcontroller unit, a digital signal processor (DSP), a field programmable gate array (FPGA), an advanced RISC machine (ARM), a programmable logic device (PLD), any circuit or processor capable of executing one or more functions, or the like, or any combination thereof.

Merely for illustration, only one processor is described in the computing device 200. However, it should be noted that the computing device 200 in the present disclosure may also include multiple processors, thus operations and/or method steps that are performed by one processor as described in the present disclosure may also be jointly or separately performed by the multiple processors. For example, if in the present disclosure the processor of the computing device 200 executes both process A and process B, it should be understood that process A and process B may also be performed by two or more different processors jointly or separately in the computing device 200 (e.g., a first processor executes process A and a second processor executes process B, or the first and second processors jointly execute processes A and B).

The storage 220 may store data/information obtained from the scanner 110, the terminal(s) 130, the storage 150, and/or any other component of the imaging system 100. In some embodiments, the storage 220 may include a mass storage, a removable storage, a volatile read-and-write memory, a read-only memory (ROM), or the like, or any combination thereof. For example, the mass storage may include a magnetic disk, an optical disk, a solid-state drives, etc. The removable storage may include a flash drive, a floppy disk, an optical disk, a memory card, a zip disk, a magnetic tape, etc. The volatile read-and-write memory may include a random access memory (RAM). The RAM may include a dynamic RAM (DRAM), a double date rate synchronous dynamic RAM (DDR SDRAM), a static RAM (SRAM), a thyristor RAM (T-RAM), and a zero-capacitor RAM (Z-RAM), etc. The ROM may include a mask ROM (MROM), a programmable ROM (PROM), an erasable programmable ROM (EPROM), an electrically erasable programmable ROM (EEPROM), a compact disk ROM (CD-ROM), and a digital versatile disk ROM, etc. In some embodiments, the storage 220 may store one or more programs and/or instructions to perform exemplary methods described in the present disclosure. For example, the storage 220 may store a program for the processing engine 120 for determining a regularization item.

The I/O 230 may input and/or output signals, data, information, etc. In some embodiments, the I/O 230 may enable a user interaction with the processing engine 120. In some embodiments, the I/O 230 may include an input device and an output device. Examples of the input device may include a keyboard, a mouse, a touch screen, a microphone, or the like, or any combination thereof. Examples of the output device may include a display device, a loudspeaker, a printer, a projector, or the like, or any combination thereof. Examples of the display device may include a liquid crystal display (LCD), a light-emitting diode (LED)-based display, a flat panel display, a curved screen, a television device, a cathode ray tube (CRT), a touch screen, or the like, or any combination thereof.

The communication port 240 may be connected to a network (e.g., the network 160) to facilitate data communications. The communication port 240 may establish connections between the processing engine 140 and the scanner 110, the terminal(s) 130, and/or the storage 150. The connection may be a wired connection, a wireless connection, any other communication connection that can enable data transmission and/or reception, and/or any combination of these connections. The wired connection may include, for example, an electrical cable, an optical cable, a telephone wire, or the like, or any combination thereof. The wireless connection may include, for example, a Bluetooth™ link, a Wi-Fi™ link, a WiMax™ link, a WLAN link, a ZigBee link, a mobile network link (e.g., 3G, 4G, 5G, etc.), or the like, or any combination thereof. In some embodiments, the communication port 240 may be and/or include a standardized communication port, such as RS232, RS485, etc. In some embodiments, the communication port 240 may be a specially designed communication port. For example, the communication port 240 may be designed in accordance with the digital imaging and communications in medicine (DICOM) protocol.

Figure 3:
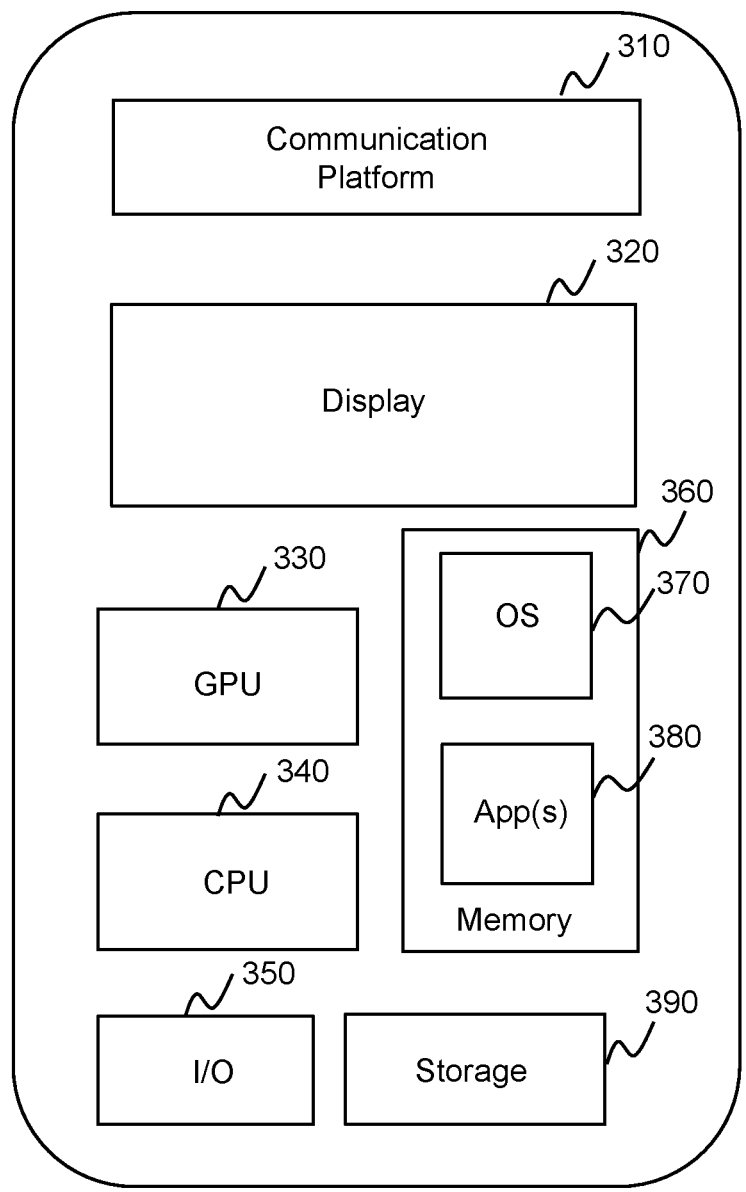
FIG. 3 is a schematic diagram illustrating exemplary hardware and/or software components of an exemplary mobile device according to some embodiments of the present disclosure.

FIG. 3 is a schematic diagram illustrating exemplary hardware and/or software components of an exemplary mobile device 300 on which the terminal(s) 130 may be implemented according to some embodiments of the present disclosure. As illustrated in FIG. 3, the mobile device 300 may include a communication platform 310, a display 320, a graphic processing unit (GPU) 330, a central processing unit (CPU) 340, an I/O 350, a memory 360, and a storage 390. In some embodiments, any other suitable component, including but not limited to a system bus or a controller (not shown), may also be included in the mobile device 300. In some embodiments, a mobile operating system 370 (e.g., iOS™, Android™, Windows Phone™, etc.) and one or more applications 380 may be loaded into the memory 360 from the storage 390 in order to be executed by the CPU 340. The applications 380 may include a browser or any other suitable mobile apps for receiving and rendering information respect to image processing or other information from the processing engine 120. User interactions with the information stream may be achieved via the I/O 350 and provided to the processing engine 120 and/or other components of the imaging system 100 via the network 160.

To implement various modules, units, and their functionalities described in the present disclosure, computer hardware platforms may be used as the hardware platform(s) for one or more of the elements described herein. A computer with user interface elements may be used to implement a personal computer (PC) or any other type of work station or external device. A computer may also act as a server if appropriately programmed.

Figure 4:
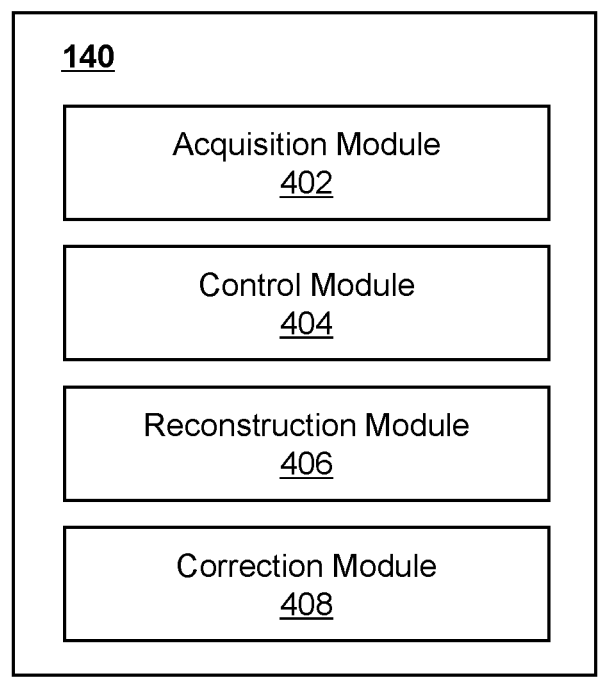
FIG. 4 is a block diagram illustrating an exemplary engine according to some embodiments of the present disclosure.

FIG. 4 is a schematic diagram illustrating an exemplary processing engine 140 according to some embodiments of the present disclosure. As shown in the figure, the processing engine 140 may include an acquisition module 402, a control module 404, a reconstruction module 406, and a correction module 408. At least a portion of the processing engine 140 may be implemented on a computing device as illustrated in FIG. 2 or a mobile device as illustrated in FIG. 3.

The acquisition module 402 may acquire image data. In some embodiments, the acquisition module 402 may acquire the image data from the scanner 110, the storage 150, the terminal(s) 130, and/or an external data source (not shown). In some embodiments, the image data may include raw data (e.g., projection data), instructions, or the like, or a combination thereof. For example, the image data may be generated based on the radiation rays (e.g., gamma rays) that emit from a subject positioned in the detection region 113. In some embodiments, the image data may include information relating to energy, an interaction position, and/or an interaction time of the radiation rays (e.g., gamma rays). The image data may include PET data. In some embodiments, the PET data may include coincidence event data, single event data, random event data, scattered event data, etc. The coincidence event data may further inlucde TOF information, non-TOF information, depth-of-interaction (DOI) information, energy information, or the like, or any informaiton thereof. In some embodiments, the PET data may be used to determine the distribution of PET tracer molecules in the image domain and/or the coincidence distribution in a sinogram. In some embodiments, the PET data may be used to determine an attenuation map of PET tracer molecules. The instructions may be executed by the processor(s) of the processing engine 140 to perform exemplary methods described in this disclosure. In some embodiments, the acquired data may be transmitted to the storage 150 for storing. In some embodiments, the acquired data may be transmitted to the reconstruction module 406 to reconstruct one or more images (e.g., an activity map, an attenuation map, etc.).

The control module 404 may control operations of the acquisition module 402, the reconstruction module 406 (e.g., by generating one or more control parameters), the correction module 408, the scanner 110, or the like, or a combination thereof. For example, the control module 404 may control the acquisition module 402 to acquire image data, the timing of the acquisition of the image data, etc. As another example, the control module 404 may control the reconstruction module 406 to process image data acquired by the acquisition module 402. As a further example, the control module 404 may control the operation of the scanner 110. In some embodiments, the control module 404 may receive a real-time instruction from an operator or retrieve a predetermined instruction provided by a user (e.g., a doctor) to control one or more operations of the scanner 110, the acquisition module 402, the reconstruction module 406, and/or the correction module 408. For example, the control module 404 may adjust the acquisition module 402 and/or the reconstruction module 406 to generate one or more images of a subject according to the real-time instruction and/or the predetermined instruction. In some embodiments, the control module 404 may communicate with one or more other modules of the processing engine 140 for exchanging information and/or data.

The reconstruction module 406 may reconstruct one or more images of a scanned object. In some embodiments, the reconstruction module 406 may reconstruct the images based on image data acquired by the acquisition module 402, and/or image data retrieved from the storage 150, etc. In some embodiments, the reconstruction module 406 may reconstruct the images according to a reconstruction technique, generate reports including one or more images and/or other related information, and/or perform any other function for image reconstruction in accordance with various embodiments of the present disclosure. The reconstruction technique may include an iterative reconstruction algorithm (e.g., a maximum likelihood expectation maximization (MLEM) algorithm, an ordered subset expectation maximization (OSEM) algorithm, a maximum-likelihood reconstruction of attenuation and activity (MLAA) algorithm, a maximum-likelihood attenuation correction factor (MLACF) algorithm, a maximum likelihood transmission reconstruction (MLTR) algorithm, a conjugate gradient algorithm, a maximum-a-posteriori estimation algorithm, a filtered back projection (FBP) algorithm, a 3D reconstruction algorithm, or the like, or any combination thereof.

The correction module 408 may correct one or more images. For example, the correction module 408 may correct the image(s) reconstructed by the reconstruction module 406, the image(s) retrieved from the storage 150, etc. In some embodiments, the correction module 408 may correct the image(s) based on one or more correction techniques. The correction technique may include a random correction, a scatter correction, an attenuation correction, a dead time correction, normalization, or the like, or any combination thereof. In some embodiments, the correction module 408 may perform one or more corrections in image reconstruction.

In some embodiments, one or more modules illustrated in FIG. 4 may be implemented in at least part of the exemplary imaging system 100 as illustrated in FIG. 1. For example, the acquisition module 402, the control module 404, the reconstruction module 406, and/or the correction module 408 may be integrated into a console (not shown). Via the console, a user may set the parameters for scanning a subject, acquiring image data, etc. In some embodiments, the console may be implemented via the processing engine 140 and/or an external device (not shown).

It should be noted that the above description of the processing engine 140 is merely provided for the purpose of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, a pre-processing module may be configured in the processing engine 140. The pre-processing module may pre-process (e.g., denoise, normalize, smooth, enhance, etc.) the image data acquired by the acquisition module 402 before reconstruction. As another example, the reconstruction module 406 and the correction module 408 may be integrated into one single module to perform their functions. As a further example, the processing engine 140 may include an output module configured to transmit the processed image to the scanner 110, the terminal(s) 130, and/or the storage 150 via the network 120.

Figure 5:
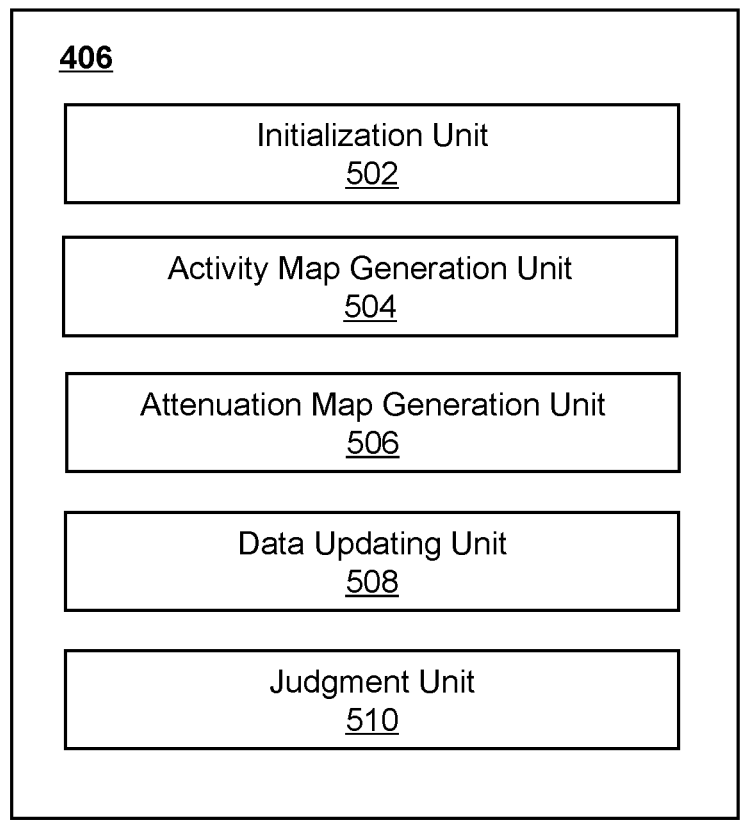
FIG. 5 is a block diagram illustrating an exemplary reconstruction module according to some embodiments of the present disclosure.

FIG. 5 is a schematic diagram illustrating an exemplary reconstruction module 406 according to some embodiments of the present disclosure. The reconstruction module 406 may include an initialization unit 502, an activity map generation unit 504, an attenuation map generation unit 506, a data updating unit 508, and a judgment unit 510. At least a portion of the reconstruction module 406 may be implemented on a computing device as illustrated in FIG. 2 or a mobile device as illustrated in FIG. 3.

The initialization unit 502 may initialize one or more images and/or parameters that may be used by the reconstruction module 406. For example, the images to be initialized may include an initial activity map, an initial attenuation map, etc. The parameters to be initialized may include an initial iteration count, a threshold, etc. In some embodiments, the initialization unit 502 may initialize the images and/or the parameters based on a user input, or a default setting of the imaging system 100.

The activity map generation unit 504 may generate an activity map. The activity map (e.g., tracer activity, activity, activity image, tracer distribution, tracer distribution image, or tracer distribution map) may be associated with a distribution of tracer molecules in a tissue of interest of a scanned subject. The activity map generation unit 504 may generate the activity map based on the image data acquired by the acquisition module 402. In some embodiments, the activity map generation unit 504 may generate the activity map based on one or more algorithms including, for example, an iterative reconstruction algorithm, a filtered back projection (FBP) algorithm, a 3D reconstruction algorithm, etc., as described elsewhere in the present disclosure.

The attenuation map generation unit 506 may generate an attenuation map. The attenuation map may be associated with a plurality of attenuation coefficients of the radiation rays emitted from the scanned subject. The attenuation map generation unit 506 may generate the attenuation map based on the image data acquired by the acquisition module 402. In some embodiments, the attenuation map generation unit 504 may generate the attenuation map based on one or more algorithms including, for example, an iterative reconstruction algorithm, a filtered back projection (FBP) algorithm, a 3D reconstruction algorithm, etc., as described elsewhere in the present disclosure.

The data updating unit 508 may update data. The data to be updated may relate to intermediate results generated by the implementation of the reconstruction module 406. For example, the data may include an estimated activity map, an estimated attenuation map, the current iteration count, etc., as described in FIGS. 7, 8, and 9. In some embodiments, the data updating unit 508 may update data based on at least one relationship. For example, the image updating unit 508 may update an estimated activity map based on a relationship that is associated with, for exmaple, single events. As another example, the data updating unit 508 may count or update the number of iterations when a current iteration is finished and a next iteration is to be started. In some embodiments, the data updated by the data updating unit 508 may be further judged by the judgment unit 510.

The judgment unit 510 may perform a judgment based on one or more images and/or parameters relating to intermediate results generated by the implementation of the reconstruction module 406. In some embodiments, the intermediate results may include an estimated activity map, an estimated attenuation map, an updated activity map, an updated attenuation map, or a current iteration count, as described in FIGS. 7, 8, and 10. In some embodiments, the judgment unit 510 may judge whether the intermediate results satisfy one or more termination criteria. The termination criteria may be determined based on a user input, or a default setting of the imaging system 100. For example, the judgment unit 510 may judge whether at least one of the estimated activity map, the estimated attenuation map, the updated activity map, and the updated attenuation map is convergent is convergent. As another example, the judgment unit 506 may judge whether a certain number of iterations have been performed. In some embodiments, the reconstruction module 406 may determine whether to terminate image reconstruction based on the judgment result of the judgment unit 510. For example, if the judgment unit 506 determines that the intermediate results are convergent, the reconstruction module 406 may terminate image reconstruction. As another example, if the judgment unit 506 determines that a certain number of iterations have been performed, the reconstruction module 406 may terminate image reconstruction.

It should be noted that the above description of the processing engine 140 is merely provided for the purpose of illustration, and not intended to limit the scope of the present disclosure. For persons having ordinary skills in the art, multiple variations and modifications may be made under the teachings of the present disclosure. However, those variations and modifications do not depart from the scope of the present disclosure. For example, a pre-processing module may be configured in the processing engine 140. The pre-processing module may pre-process (e.g., denoise, normalize, smooth, enhance, etc.) the image data acquired by the acquisition module 402 before reconstructing. As another example, the reconstruction module 406 and the correction module 408 may be integrated into one single module to perform their functions. As a further example, the processing engine 140 may include an output module configured to transmit the processed image to the scanner 110, the terminal(s) 130, and/or the storage 150 via the network 120.

Figure 6:
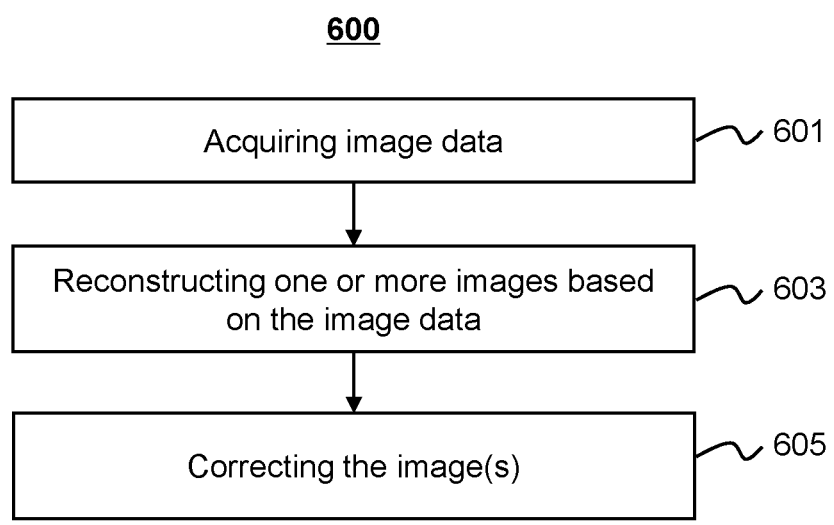
FIG. 6 is a flowchart illustrating an exemplary process for determining an image according to some embodiments of the present disclosure.

FIG. 6 is a flowchart illustrating an exemplary process 600 for generating an image according to some embodiments of the present disclosure. In some embodiments, one or more operations of the process 600 illustrated in FIG. 6 for generating an image may be implemented in the imaging system 100 illustrated in FIG. 1. For example, the process 600 illustrated in FIG. 6 may be stored in the storage 150 in the form of instructions, and invoked and/or executed by the processing engine 140 (e.g., the processor 210 of the computing device 200 as illustrated in FIG. 2, the CPU 340 of the mobile device 300 as illustrated in FIG. 3).

In 601, image data may be acquired. Operation 601 may be implemented by the acquisition module 402. In some embodiments, the image data may be acquired by the acquisition module 402 from, for example, a PET system (e.g., the imaging system 100 in FIG. 1), the scanner 110, the terminal(s) 130, the storage 150, or an external data source. In some embodiments, during a PET scan or analysis, PET tracer (also referred to as "PET tracer molecules") may be first introduced into the subject before an imaging process begins. During the PET scan, the PET tracer molecules may emit positrons, namely the antiparticles of electrons. A positron has the same mass and the opposite electrical charge as an electron, and it undergoes an annihilation (also referred to as an "annihilation event" or a "coincidence event") with an electron (that may naturally exist in abundance within the subject) as the two particles collide. An electron-positron annihilation may result in two 511 keV gamma photons, which, upon their own generation, begin to travel in opposite directions with respect to one another. The line connecting the two gamma photons may be referred to as a "line of response (LOR)." The acquisition module 402 may obtain the trajectory and/or information of the gamma photons (also referred to as the "PET data"). For example, the PET data may include a list of annihilation events, transverse and longitudinal positions of the LORs, or the like, or any combination thereof. In some embodiments, the PET data acquired may be attenuated. The attenuation of the PET data may relate to the effect of Compton scattering and/or photoelectric absorption of photons in the scanned subject. In some embodiments, the PET scan may include 2D mode and 3D mode. 2D mode may be different from the 3D mode because of connection between detector rings of the detector 112. In some embodiments, the image data acquired may be stored in a 2D matrix (i.e., a sinogram). The two demission of the matrix may respect represent the LOR angle and the distance between the LOR and the central point.

In some embodiments, the image data may be data of an object. The object may include a substance, a tissue, an organ, a specimen, a body, or the like, or any combination thereof. In some embodiments, the object may include a patient or a part thereof. The objet may include a head, a breast, a lung, a pleura, a mediastinum, an abdomen, a long intestine, a small intestine, a bladder, a gallbladder, a triple warmer, a pelvic cavity, a backbone, extremities, a skeleton, a blood vessel, or the like, or any combination thereof.

In 603, one or more images may be reconstructed based on the image data acquired in 601. Operation 603 may be implemented by the reconstruction module 406. In some embodiments, the image(s) may be reconstructed based on one or more reconstruction techniques mentioned elsewhere in the disclosure. For example, the image may be reconstructed based on one or more iterative reconstruction algorithms. In some embodiments, the iterative reconstruction algorithms may include a maximum likelihood expectation maximization (MLEM) algorithm, an ordered subset expectation maximization (OSEM) algorithm, maximum-likelihood reconstruction of attenuation and activity (MLAA) algorithm, a maximum-likelihood attenuation correction factor (MLACF) algorithm, a maximum likelihood transmission reconstruction (MLTR) algorithm, a conjugate gradient algorithm, a maximum-a-posteriori estimation algorithm, or the like, or any combination thereof. In some embodiments, the reconstructed image(s) may include an activity map and/or an attenuation map. More descriptions of the image reconstruction may be found elsewhere in the present disclosure. See, for example, FIGS. 7, 8, 9 and the description thereof.

In 605, the image(s) reconstructed in 603 may be corrected. Operation 605 may be implemented by the correction module 408. In some embodiments, the image(s) may be corrected based on one or more correction techniques mentioned in the disclosure.

It should be noted that the above description of the process 600 is merely provided for the purpose of illustration, and not intended to limit the scope of the present disclosure. For persons having ordinary skills in the art, multiple variations and modifications may be made to the process 600 under the teachings of the present disclosure. However, those variations and modifications do not depart from the scope of the present disclosure. For example, operation 603 and operation 605 may be integrated into one single operation. As another example, an image pre-processing operation may be added before operation 603. In some embodiments, the pre-processing may include noise reduction. The noise may be caused by at least one of various factors including, for example, efficiency of detectors, sensitivity of detectors, dead time prosperity, etc. The noise reduction may be performed base on algorithms including filtering, data transforming, data cleaning, or the like, or any combination thereof.

Figure 7:
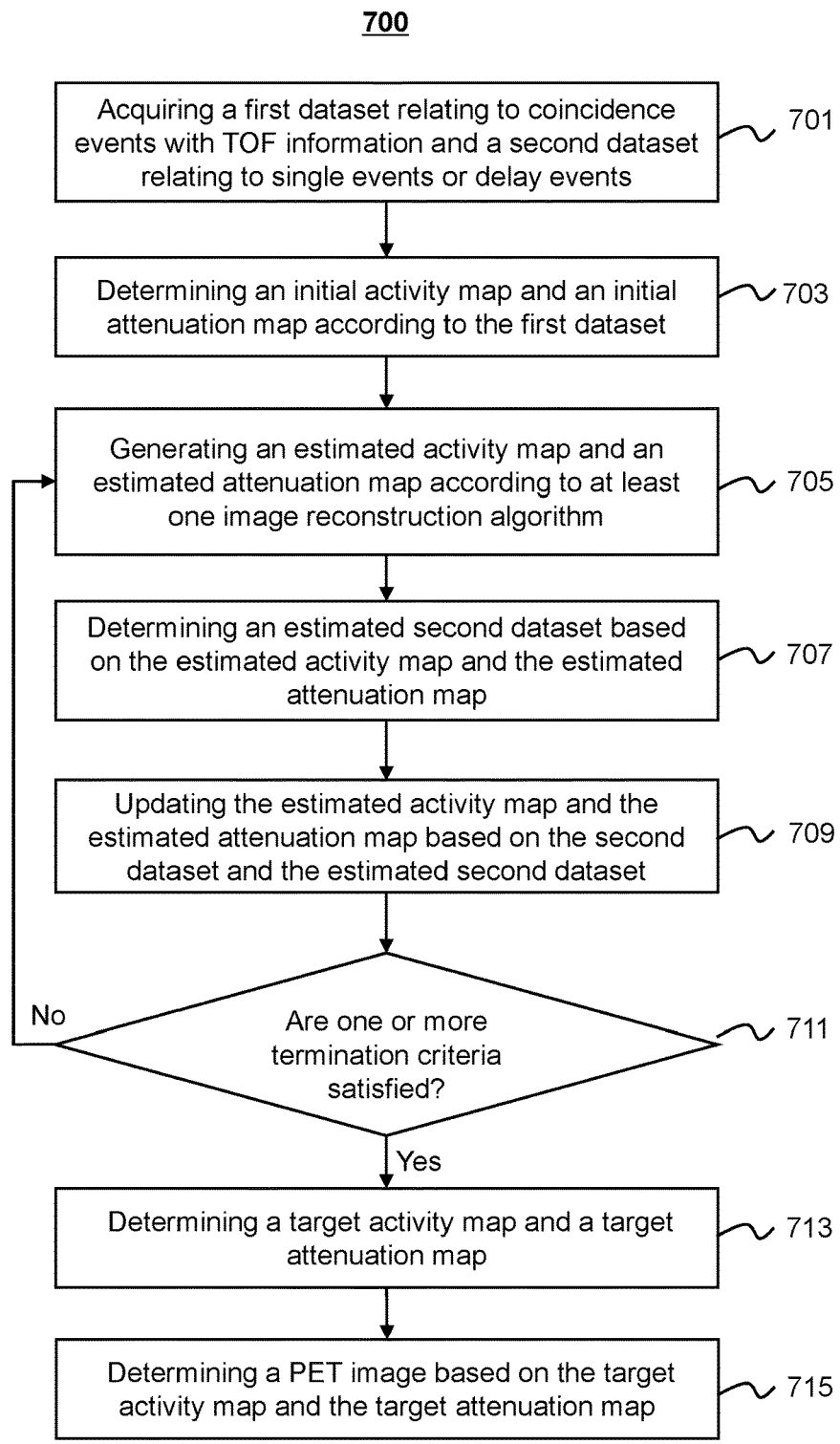
FIG. 7 is a flowchart illustrating an exemplary process for determining an image according to some embodiments of the present disclosure.

FIG. 7 is a flowchart illustrating an exemplary process 700 for generating an image according to some embodiments of the present disclosure. In some embodiments, one or more operations of the process 700 illustrated in FIG. 7 for generating an image may be implemented in the imaging system 100 illustrated in FIG. 1. For example, the process 700 illustrated in FIG. 7 may be stored in the storage 150 in the form of instructions, and invoked and/or executed by the processing engine 140 (e.g., the processor 210 of the computing device 200 as illustrated in FIG. 2, the CPU 340 of the mobile device 300 as illustrated in FIG. 3).

In 701, a first dataset relating to coincidence events with TOF information and a second dataset relating to single events or delay events may be acquired. Operation 701 may be performed by the acquisition module 402. In some embodiments, the first dataset may be stored in the storage 150 as a sinogram. TOF information may include the precise time points that one or more of the coincident photons (e.g., each of the coincident photons) in the coincidence events are detected. In some embodiments, TOF may depend on the speed of light c and the distance that the coincident photons travel. A difference between the precise time points that two coincident photons in a coincidence event are detected may be determined, and thus, a location of the annihilation along the LOR between the two detector units that detect the coincidence event may be determined. In some embodiments, the single events may include a plurality of events (e.g., all events) detected in a PET scan. For example, the single events may include the two detected photon events in coincidence events. The single events may also include all events prior to coincidence detection or designation. In some embodiments, the second dataset may include delay events. In some embodiments, the delay events may include the coincidence events detected with an artificially determined time delay.

In some embodiments, the first dataset and the second dataset may be acquired sequentially or simultaneously. For example, the first dataset may be acquired prior to, later than, or at the same time as the acquisition of the second dataset. In some embodiments, the first dataset and the second dataset may be acquired based on data from the same PET scan. In some embodiments, the second dataset may include the first dataset. In some embodiments, the first dataset may be a subset of the second dataset. For example, the first dataset may be acquired by adding a coincidence window from the second dataset.

In 703, an initial activity map and an initial attenuation map may be determined according to the first dataset. Operation 703 may be performed by the initialization unit 502 of the reconstruction module 406. In some embodiments, the initialization unit 502 may assign each pixel value of the initial activity map and/or the initial attenuation with any value, for example, 0, 0.25, 0.5, 0.75, 1, etc. In some embodiments, before the initialization operation, a boundary or a boundary image indicating an edge of the subject may be determined. The boundary of the initial activity map and/or the initial attenuation map may be in accordance with the boundary of the subject. For example, the initialization unit 502 may determine a plurality of data points associated with the boundary, and then the data points of the initial activity map and/or the initial attenuation map may be assigned with the pixel values within the boundary. In some embodiments, at least part of the boundary of the initial activity attenuation map may be different from at least part of the boundary of the initial attenuation map. In some embodiments, the initial activity attenuation map and the initial attenuation map may share a common boundary.

In 705, an estimated activity map and an estimated attenuation map may be generated according to at least one image reconstruction algorithm. Operation 705 may be performed by the activity map generation unit 504 and the attenuation map generation unit 506 of the reconstruction module 406. In some embodiments, operation 705 may be based on the initial activity map and the initial attenuation map determined in operation 703 or based on an updated activity map and an updated attenuation map obtained in operation 709 in a previous iteration. In some embodiments, at least one image reconstruction algorithm be iterative reconstruction algorithms including, for example, the iterative reconstruction algorithms may include a maximum likelihood expectation maximization (MLEM) algorithm, an ordered subset expectation maximization (OSEM) algorithm, a maximum-likelihood reconstruction of attenuation and activity (MLAA) algorithm, a maximum-likelihood attenuation correction factor (MLACF) algorithm, a maximum likelihood transmission reconstruction (MLTR) algorithm, a conjugate gradient algorithm, a maximum-a-posteriori estimation algorithm, or the like, or any combination thereof. Detailed description of the image reconstruction algorithm may be found elsewhere in the present disclosure, see, for example, process 800 in FIG. 8.

In 707, an estimated second dataset may be determined based on the estimated activity map and the estimated attenuation map. Operation 707 may by performed by the reconstruction module 406. In some embodiments, the estimated second dataset may be related to single events or delay events that calculated by at one or more equations relating to the estimated activity map and the estimated attenuation map. Detailed description of the estimated second dataset determination may be found elsewhere in the present disclosure, see, for example, process 900 in FIG. 9.

In 709, the estimated activity map and the estimated attenuation map may be updated to obtain an updated activity map and an updated attenuation map based on the second dataset and the estimated second dataset. Operation 709 may be performed by the data updating unit 508 of the reconstruction module 406. In some embodiments, the updated activity map and the updated attenuation map may be obtained according to at least one relationship relating to the second dataset and the estimated second dataset. For example, there may be a first relationship used to update the estimated activity map and a second relationship used to update the estimated attenuation. In some embodiments, the relationship may be expressed as a function, an equation, an algorithm, a formula, a map, or the like, or any combination thereof. The relationship may be linear or non-linear. Merely taking the relationship expressed by a function as an example, it may include a linear function, a quadratic function, a trigonometric function, an exponential function, a logarithmic function, a power function, or the like, or any combination thereof. Detailed descriptions of the operation 709 may be found elsewhere in the present disclosure. See, for example, process 900 in FIG. 9.

In 711, whether one or more termination criteria are satisfied may be judged by the judgment unit 510 of the reconstruction module 406. In some embodiments, the termination criteria may include at least one of the estimated activity map, the estimated attenuation map, the updated activity map, and the updated attenuation map is convergent, or an iteration count of the plurality of iterations exceeds a predetermined threshold. The term "convergent" used herein may represent a condition that the values of the updated activity map and/or the updated attenuation map became exactly or approximately stable after a plurality of iterations. The convergent condition may usually be corresponding to an optimal solution of the updated activity map or the updated attenuation map. In some embodiments, the convergent condition may be a global convergence, a semi-global convergence, or a local convergence, etc. In some embodiments, the convergent condition may be compared with a first predetermined threshold. For example, if the difference between updated activity maps (and/or difference between updated attenuation maps) in two or more consecutive iterations meets the first predetermined threshold, the updated activity map (and/or the updated attenuation map) may be regarded as convergent. In some embodiments, to achieve the convergent condition, the differences between each two or more consecutive iterations may further be needed to meet the predetermined threshold for several times consistently. The first predetermined threshold may be set based on a user input, or a default setting of the imaging system 100. For example, the first predetermined threshold may be any value in absolute terms (e.g., 0.001, 0.01, or 0.1) or a relative value (e.g., 0.1%, 1%, or 10%).

In some embodiments, the convergent condition may be replaced by judging whether the iteration count of the process 700 exceeds a second predetermined threshold. The second predetermined threshold may be predetermined based on a user input, or a default setting of the imaging system 100. For example, the second predetermined threshold may be any value, e.g., 10 times, 50 times, 100 times. In some embodiments, the convergent condition may be replaced by judging whether the change of the average value of pixels or voxels in the updated attenuation maps and/or the updated attenuation maps generated in two or more consecutive iterations exceeds a third predetermined threshold. The third predetermined threshold may be set based on a user input, or a default setting of the imaging system 100. For example, the third predetermined threshold may be any value in absolute terms (e.g., 0.001, 0.01, or 0.1) or a relative value (e.g., 0.1%, 1%, or 10%).

In some embodiments, the estimated activity map and/or the estimated attenuation map determined in 705 may also be judged as to whether they are convergent. The judgment may be performed similar to the convergence judgment of the updated activity map and/or the updated attenuation map as described above and are not repeated here.

If the one or more termination criteria are not satisfied, the processing engine 140 may resume performing operation 703 in a next iteration, e.g., to regenerate an estimated activity map and an estimated attenuation map based on the updated activity map and the updated attenuation map in 709. Detailed description may be found elsewhere in the present disclosure. See, for example, process 800 in FIG. 8.

If the one or more termination criteria are satisfied, the process 700 may proceed to 713 to determine a target activity map and a target attenuation map. For example, the updated activity map and the updated attenuation map determined in 709 may be regarded as the target activity map and the target attenuation map to produce a PET image.

In 715, a PET image may be determined based on the target activity map and the target attenuation map. Operation 715 may be performed by reconstruction module 406 of the processing engine 140. In some embodiments, to generate the PET image, the target activity map may be corrected by the target attenuation map.

It should be noted that the above description of the process 700 is merely provided for the purpose of illustration, and not intended to limit the scope of the present disclosure. For persons having ordinary skills in the art, multiple variations and modifications may be made to the process 700 under the teachings of the present disclosure. However, those variations and modifications do not depart from the scope of the present disclosure. For example, operation 701 may be divided into two operations. In some embodiments, the first dataset and the second dataset may be pre-processed (e.g., filtered, de-noised, classified, or sorted) by the processing engine 130. In some embodiments, in 701, other data may be acquired instead of the second dataset relating to the single events. The data acquired in 701 may be any measured data decided by the plurality of single events. For example, the measured data may be contributed by a plurality of delay events. The delay events may be the estimate of random events, and random events may have a positive correlation with the single events, and thus, the delay events may be positively correlated with the single events. Therefore, the target activity map and the target attenuation map may be determined based on the delay events and the TOF information. As a further example, the reconstructed image obtained at 715 may be corrected in terms of, e.g., a random correction, a scatter correction, an attenuation correction, a dead time correction, normalization, or the like, or any combination thereof. The correction may be performed by the correction module 408.

Figure 8:
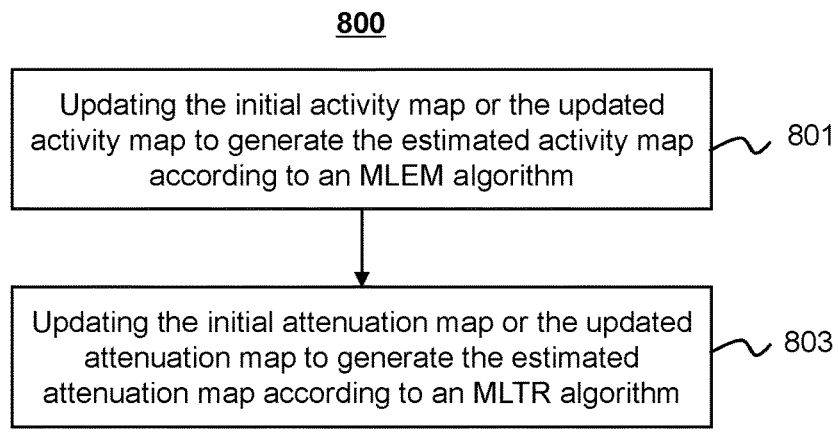
FIG. 8 is a flowchart illustrating an exemplary process for determining an estimated activity map and an estimated attenuation map according to some embodiments of the present disclosure.

FIG. 8 is a flowchart illustrating an exemplary process for determining an estimated activity map and an estimated attenuation map according to some embodiments of the present disclosure. In some embodiments, one or more operations of the process 800 illustrated in FIG. 8 for generating the estimated activity map and the estimated activity map may be implemented in the imaging system 100 illustrated in FIG. 1. For example, the process 800 illustrated in FIG. 8 may be stored in the storage 150 in the form of instructions, and invoked and/or executed by the processing engine 140 (e.g., the processor 210 of the computing device 200 as illustrated in FIG. 2, the CPU 340 of the mobile device 300 as illustrated in FIG. 3).

In 801, an estimated activity map may be generated by updating the initial activity map or the updated activity map. Operation 801 may be performed by the activity map generation unit 504 of the reconstruction module 406. Assuming that in the $n^{th}$ iteration of the process 700, the estimated activity map may be remarked as f'′. In some embodiments, the estimated activity map f'′ may be generated based on an iterative reconstruction algorithm, for example, a maximum likelihood expectation maximization (MLEM) algorithm, an ordered subset expectation maximization (OSEM) algorithm, etc.

Taking the MLEM algorithm as an example, the estimated activity map f'′ may be generated based on the at least one subset of the first dataset, and an updated activity map $f^{(n-1)\prime}$ generated in a previous iteration. If in the first iteration, $f^{0\prime}$ may be the initial activity map determined in 703. In some embodiments, the generation of the estimated activity map f'′ may be illustrated as Equation (1):

$$f_j^{(n,m+1)} = \frac{f_j^{(n,m)}}{\sum_{t,i \in S_m} \overline{a}_i^{(n,m)} H_{ijt}} \sum_{t,i \in S_m} H_{ijt} \frac{1/\varepsilon_i(t)}{\sum_{k,t} H_{ikt} f_k^{(n,m)} + \frac{s_i(t) + r_i(t)}{\overline{a}_i^{(n,m)}}}, \quad (1)$$

where $f_j^{(n,m+1)}$ may represent an estimated activity map in the $n^{th}$ iteration using $(m+1)^{th}$ subset of the first dataset, $f_j^{(n,m)}$ may represent an estimated activity map in the $n^{th}$ iteration using $m^{th}$ subset of the first dataset relating to coincidence events, $S_m$ may represent the $m^{th}$ subset of the first dataset relating to coincidence events, $H_{ijt}$ and $H_{ikt}$ may represent a system response matrix of the imaging system 100, i may indicate a serial number of LORs, k or j may represent a $k^{th}$ or $j^{th}$ voxel in the updated estimated activity map $f^{(n-1)\prime}$, t may represent the time bin of TOF technique, $\varepsilon_i(t)$ may represent a correction factor for the data of the $i^{th}$ LOR and the $t^{th}$ time bin, $s_i(t)$ may represent the number of scattering events for the data of the $i^{th}$ LOR and the $t^{th}$ time bin, $r_i(t)$ may represent the number of random events for the data of the $i^{th}$ LOR and the $t^{th}$ time bin, and $\overline{a}_i^{(n,m)}$ may represent an estimated attenuation map in the $n^{th}$ iteration using $m^{th}$ subset of the first dataset relating to coincidence events. In some embodiments, the system response matrix may indicate the contribution of photons to an image (e.g., an activity map). $H_{ijt}$ and $H_{ikt}$ may be the same matrix illustrated by different subscripts j and k.

In some embodiments, the generation of the estimated activity map may be determined by keeping the attenuation map as a constant. For example, in the first iteration, the attenuation map used in 801 may be the initial attenuation map $\mu^0$ determined in 703. In the $n^{th}$ iteration, the attenuation map used in 801 may be an updated attenuation map $\mu^{(n-1)\prime}$ generated in the previous iteration. In some embodiments, the estimated activity map in operation 801 may be generated through an iterative procedure. For example, the estimated activity map may be determined after a series of iterations to meet one or more termination criteria. The termination criteria may include the estimated activity map is convergent or an iteration count of the iterative procedure exceeds a fourth predetermined threshold. The fourth predetermined threshold may be predetermined based on a user input, or a default setting of the imaging system 100. For example, the fourth predetermined threshold may be any value, e.g., 10 times, 50 times, 100 times.

In 802, an estimated attenuation map μ'′ may be determined. Operation 802 may be performed by the attenuation map generation unit 504 of the reconstruction module 406. In some embodiments, the estimated attenuation map μ'′ may be determined according to an iterative reconstruction algorithm, for example, a maximum likelihood transmission reconstruction (MLTR) algorithm. Using the MLTR algorithm, the estimated attenuation map μ'′ may be updated based on the at least one subset of the second dataset relating to single events and an updated attenuation map $\mu^{(n-1)\prime}$ generated in a previous iteration. If in the first iteration, $\mu^0$ may be initial attenuation map determined in 703. In some embodiments, the generation of the estimated attenuation map μ'′ may be illustrated as Equation (2):

$$\mu_j^{(n,m+1)} = \mu_j^{(n,m)} + \frac{\sum_{i \in S_m} l_{ij} \frac{\overline{y}_i^{(n,m+1)}}{\overline{y}_i^{(n,m+1)} + s_i + r_i} (y_i^{(n,m+1)} + s_i + r_i - y_i)}{\sum_{i \in S_m} l_{ij} \frac{(\overline{y}_i^{(n,m+1)})^2}{\overline{y}_i^{(n,m+1)} + s_i + r_i} \sum_k l_{ik}}, \quad (2)$$

where $\mu_j^{(n,m+1)}$ may represent an estimated attenuation map in the $n^{th}$ iteration using $(m+1)^{th}$ subset of the second dataset relating to single events, $\mu_j^{(n,m)}$ may represent an estimated attenuation map in the $n^{th}$ iteration using $m^{th}$ subset of the second dataset relating to single events, $S_m$ may represent the $m^{th}$ subset of the second dataset relating to single events, $l_{ij}$ and $l_{ik}$ may represent a matrix of a line integral for mapping an attenuation map to a plurality of attenuation coefficients, i may indicate a serial number of LORs, $y_i$ may represent the number of annihilation photon pairs in the $i^{th}$ LOR, $s_i$ may represent the number of scattering events in the $i^{th}$ LOR, $r_i$ may represent the number of random events in the $i^{th}$ LOR, $\overline{y}_i^{(n,m+1)}$ may represent an expected value of the $i^{th}$ voxel of an estimated activity map in a sinogram without TOF information in the $n^{th}$ iteration using $(m+1)^{th}$ subset of the second dataset relating to single events.

In some embodiments, the generation of the estimated attenuation map μ'′ may be determined by keeping the activity map as a constant. For example, in the first iteration, the activity map used in 803 may be the initial activity map $f^0$ determined in 703. In the $n^{th}$ iteration, the activity map may be the estimated activity map f'′ generated in the present iteration. In some embodiments, the estimated attenuation map in operation 802 may be generated through an iterative procedure. For example, the estimated attenuation map may be determined after a series of iterations to meet one or more termination criteria. The termination criteria may include the estimated attenuation map is convergent or an iteration count of the iterative procedure exceeds a fifth predetermined threshold. The fifth predetermined threshold may be predetermined based on a user input, or a default setting of the imaging system 100. For example, the fifth predetermined threshold may be any value, e.g., 10 times, 50 times, 100 times.

It should be noted that the above description of the process 800 is merely provided for the purpose of illustration, and not intended to limit the scope of the present disclosure. For persons having ordinary skills in the art, multiple variations and modifications may be made to the process 800 under the teachings of the present disclosure. However, those variations and modifications do not depart from the scope of the present disclosure. In some embodiments, the Equation (1) or (2) may be modified. For example, each parameter in the Equation (1) or (2) may be replaced or dropped, e.g., the Equation (1) may not rely on the updated activity map generated in a previous iteration.

Figure 9:
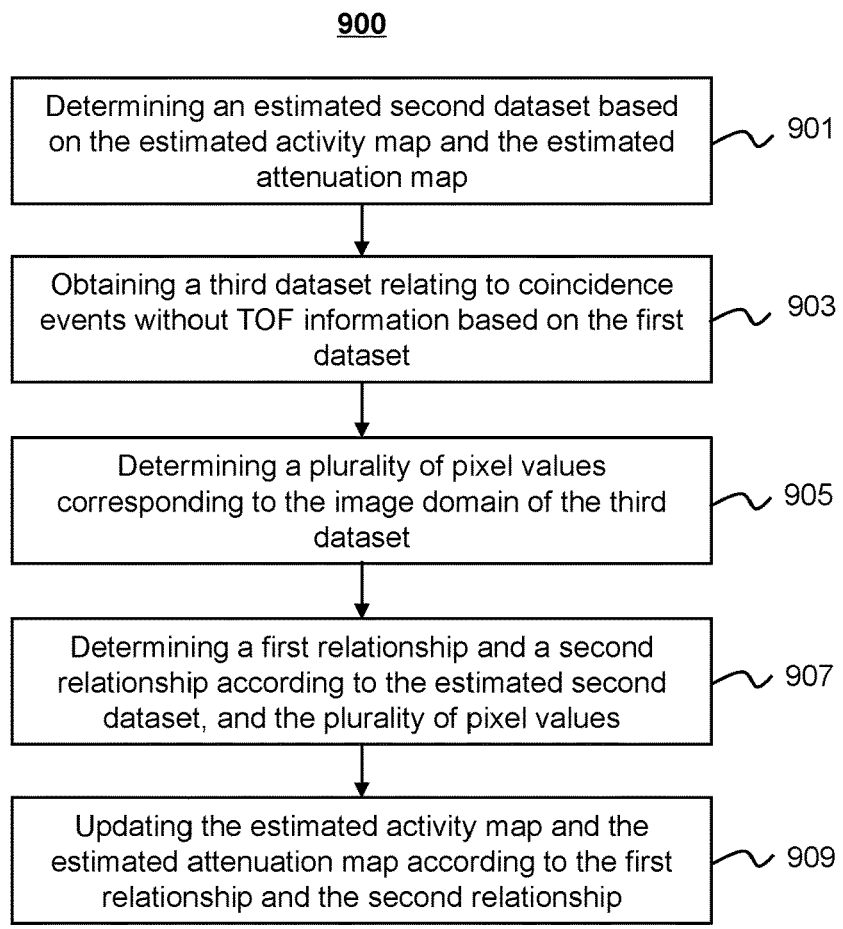
FIG. 9 is a flowchart illustrating an exemplary process for updating an estimated activity map and an estimated attenuation map according to some embodiments of the present disclosure.

FIG. 9 is a flowchart illustrating an exemplary process 900 for updating an estimated activity map and an estimated attenuation map according to some embodiments of the present disclosure. In some embodiments, one or more operations of the process 900 illustrated in FIG. 9 for updating the estimated activity map and the estimated attenuation map may be implemented in the imaging system 100 illustrated in FIG. 1. For example, the process 800 illustrated in FIG. 8 may be stored in the storage 150 in the form of instructions, and invoked and/or executed by the processing engine 140 (e.g., the processor 210 of the computing device 200 as illustrated in FIG. 2, the CPU 340 of the mobile device 300 as illustrated in FIG. 3).

In 901, an estimated second dataset may be determined based on the estimated activity map and the estimated attenuation map generated in the process 800. Operation 901 may be performed by the reconstruction module 406. In the $n^{th}$ iteration of the process 700, for a detector unit located at angle θ (see, e.g., FIG. 10B) in the detector ring of the detector 112, $\tilde{\mathbb{S}}(\theta)^n$ relating to recorded single events may be expressed as Equation (3):

$$\tilde{\mathbb{S}}^{(n)}(\theta) = \iint_{All} G^{(n)}(s,\varphi) h(s,\varphi,\theta) ds d\varphi, \quad (3)$$

where h(s, φ, θ) equals 1 if and only if the LOR at (s, φ) is detected by the detector unit located at angle θ. Otherwise, h(s, φ, θ)=0. Detailed description may be found in FIG. 10B. In some embodiments, the recorded single events expressed in Equation (3) may include recorded coincidence events. G(s, φ) may represent image data relating to single events for one LOR, if scattering events and random events are neglected, may be expressed as Equation (4):

$$G^{(n)}(s,\varphi) = \iint_{All} E * f^{(n)}(x,y) \delta(x\cos(\varphi)+y\sin(\varphi)-s) * \exp(-A(s,\varphi,y\cos(\varphi)-x\sin(\varphi))) dx dy, \quad (4)$$

where E may be a correction factor for the efficiency of the detector 112. For example, if the probability for the detector 112 to detect a photon is 60%, and the probability for the detector 112 to detect a coincidence event is 36%, then E may be a ratio of the above probabilities, e.g., 60%/36%=5/3. For example, if the probability for a tracer molecule D to generate a positron is 50%, and the probability for the tracer molecule D to generate gamma photons is 50%, then E may be 1.5. In some embodiments, E may be always positive. $f^{(n)}(x, y)$ may be the estimated activity map $f^{(n)}$ determined in 801 that represents the activity distribution in the image domain (e.g., the x-y plane), (x,y) may be the coordinates of the image domain, s and φ are the coordinates of the sinogram domain as described in FIG. 10A, and δ(t) may be the Dirac delta function. A(s, φ, y cos(φ)−x sin(φ)) is an attenuation sinogram from a depth y cos(φ)−x sin(φ), and may be modeled as Equation (5):

$$A(s,\varphi,y\cos(\varphi)-x\sin(\varphi)) = \iint_{All} \mu^{(n)}(x,y) \delta(x\cos(\varphi)+y\sin(\varphi)-s) U((y\cos(\varphi)-x\sin(\varphi))-y\cos(\varphi)-x\sin(\varphi))) dx dy, \quad (5)$$

where U(t) is a step function. U(t) may be 1 if t≥0. U(t) may be 0 if t<0. $\mu^{(n)}(x,y)$ may be the estimated attenuation map $\mu^{(n)}$ determined in 803.

Using Equations (3), (4), and (5), the estimated activity map $f^{(n)}$, and the estimated attenuation map $\mu^{(n)}$, the estimated $\tilde{\mathbb{S}}^{(n)}(\theta)$ relating to the single events acquired by detector unit located at angle θ may be determined. Then the estimated second dataset may be determined by integrating $\tilde{\mathbb{S}}^{(n)}(\theta)$ together on the whole angles, e.g., $\int \tilde{\mathbb{S}}^{(n)}(\theta) d(\theta)$.

In 903, a third dataset relating to coincidence events without TOF information may be obtained. Operation 903 may be performed by the reconstruction module 406. In some embodiments, the third dataset may be calculated from the first dataset, for example, by summing the data in the first dataset in r direction.

In 905, a plurality of pixel values d(x, y) corresponding to the image domain of the third dataset may be determined. Operation 905 may be performed by reconstruction module 406.

In 907, a first relationship and a second relationship may be determined based on the estimated second dataset $\tilde{\mathbb{S}}^{(n)}(\theta)$ and the plurality of pixel values d(x,y). Operation 907 may be performed by the reconstruction module 406. In some embodiments, the first relationship and the second relationship may be equations or functions to update the estimated activity map $f^{(n)}$ and the estimated map $\mu^{(n)}$. Merely by way of example, the first relationship may be expressed as Equation (6) below:

$$f^{(n)'} = f^{(n)} * \frac{\int \mathbb{S}(\theta) d\theta}{\int \tilde{\mathbb{S}}^{(n)}(\theta) d\theta}, \quad (6)$$

where $f^{(n)'}$ represents an updated activity map generated by updating the estimated activity map $f^{(n)}$, $\int \mathbb{S}(\theta)d(\theta)$ represents the second dataset acquired in 701, and $\int \tilde{\mathbb{S}}^{(n)}(\theta) d(\theta)$ represents the estimated second dataset.

The second relationship may be expressed as Equation (7) below:

$$\mu^{(n)'}(x,y) = \mu^{(n)}(x,y) + \log\left(\frac{\int \mathbb{S}(\theta) d\theta}{\int \tilde{\mathbb{S}}^{(n)}(\theta) d\theta}\right) d(x,y), \quad (7)$$

where $\mu^{(n)'}(x,y)$ represents an updated attenuation map generated by updating the estimated attenuation map $\mu^{(n)}$ or $\mu^{(n)}(x,y)$, $\int \mathbb{S}(\theta)d(\theta)$ represents the second dataset acquired in 701, and $\int \tilde{\mathbb{S}}^{(n)}(\theta) d(\theta)$ represents the estimated second dataset, and d(x,y) represents the plurality of pixel values corresponding to the image domain of the third dataset.

As described above, the first relationship and the second relationship may include a ratio of the second dataset $\int \mathbb{S}(\theta)d(\theta)$ to the estimated second dataset $\int \tilde{\mathbb{S}}^{(n)}(\theta) d(\theta)$. In some embodiments, the second dataset $\int \mathbb{S}(\theta)d(\theta)$ and the estimated second dataset $\int \tilde{\mathbb{S}}^{(n)}(\theta) d(\theta)$ may be used by other modifications, for example, using their absolute difference $|\int \tilde{\mathbb{S}}^{(n)}(\theta) d(\theta) - \int \mathbb{S}(\theta)d(\theta)|$, relative difference $|\int \tilde{\mathbb{S}}^{(n)}(\theta) d(\theta) - \int \mathbb{S}(\theta)d(\theta)|/\int \tilde{\mathbb{S}}^{(n)}(\theta) d(\theta)$, etc.

In 909, the estimated activity map and the estimated attenuation map may be updated according to the first relationship and the second relationship. Operation 909 may be performed by the data updating unit 508 of the reconstruction module 406. In some embodiments, as described in 907, the estimated activity map $f^{(n)}$ may be updated according to the first relationship to generate an updated activity map $f^{(n)'}$. The estimated attenuation map $\mu^{n}$ or $\mu^{(n)}(x,y)$ may be updated by the second relationship to generate an updated attenuation map $\mu^{(n)'}$ or $\mu^{(n)'}(x, y)$.

It should be noted that the above description of the process 900 is merely provided for the purpose of illustration, and not intended to limit the scope of the present disclosure. For persons having ordinary skills in the art, multiple variations and modifications may be made to the process 800 under the teachings of the present disclosure. However, those variations and modifications do not depart from the scope of the present disclosure. For example, operations 903 and 905 may be performed before operation 901. As another example, operation 901, 903, and 905 may be integrated into one single operation. As a further example, operation 907 may be performed before operation 909. As a further example, operation 907 and operation 909 may be integrated into one single operation.

Figure 10A:
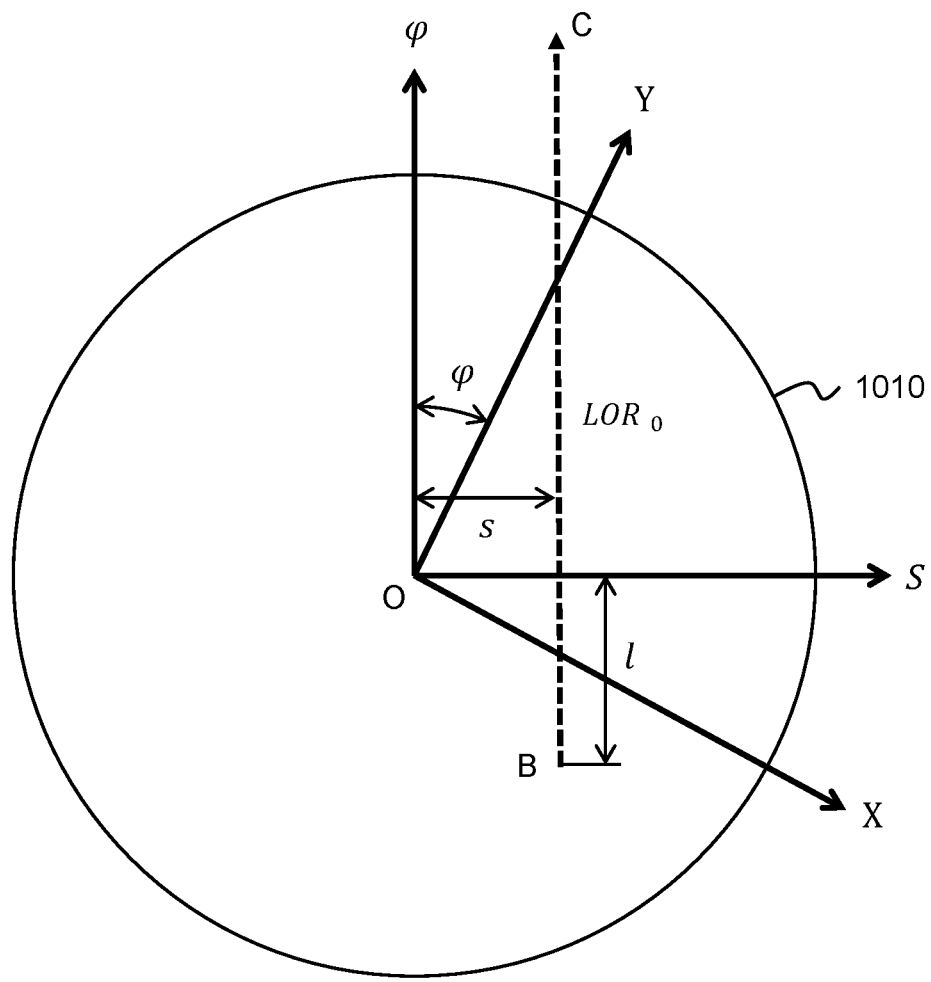
FIG. 10A is a schematic diagram illustrating an exemplary depth l according to some embodiments of the present disclosure.

FIG. 10A is a schematic diagram illustrating an exemplary depth l according to some embodiments of the present disclosure. As illustrated in FIG. 10A, a transverse scan field 1010 of the detector 112 may have a center point O. The transverse scan field 1010 may have a two-dimensional reference coordinate system, for example, the X-Y plane as illustrated in FIG. 10A. A line of response $LOR_0$ may be defined by a distance (s) of the $LOR_0$ from the center point O of the transverse scan field 1010, and an angle of orientation ($\varphi$) of the $LOR_0$ (i.e., the angle between $LOR_0$ and the vertical axis Y, also the angle between the line S that is vertical to the $LOR_0$ and the horizontal axis X). In some embodiments, a single event may start at a point B in the $LOR_0$, i.e., a photon may be emitted at the point B, and then the photon may travel along the $LOR_0$ in a direction indicated by the arrow C and strike a detector unit (not shown). The depth l may refer to a distance of the starting point B from the line S that is vertical to the $LOR_0$. In some embodiments, the depth l may indicate a starting point (e.g., the starting point B) for a line integral along the direction indicated by the arrow C. A line integral may produce projection data. A plurality of projection data produced by a plurality of line integrals in various LORs (with various s and $\varphi$ values) may constitute an attenuation sinogram A(s, $\varphi$, l).

Figure 10B:
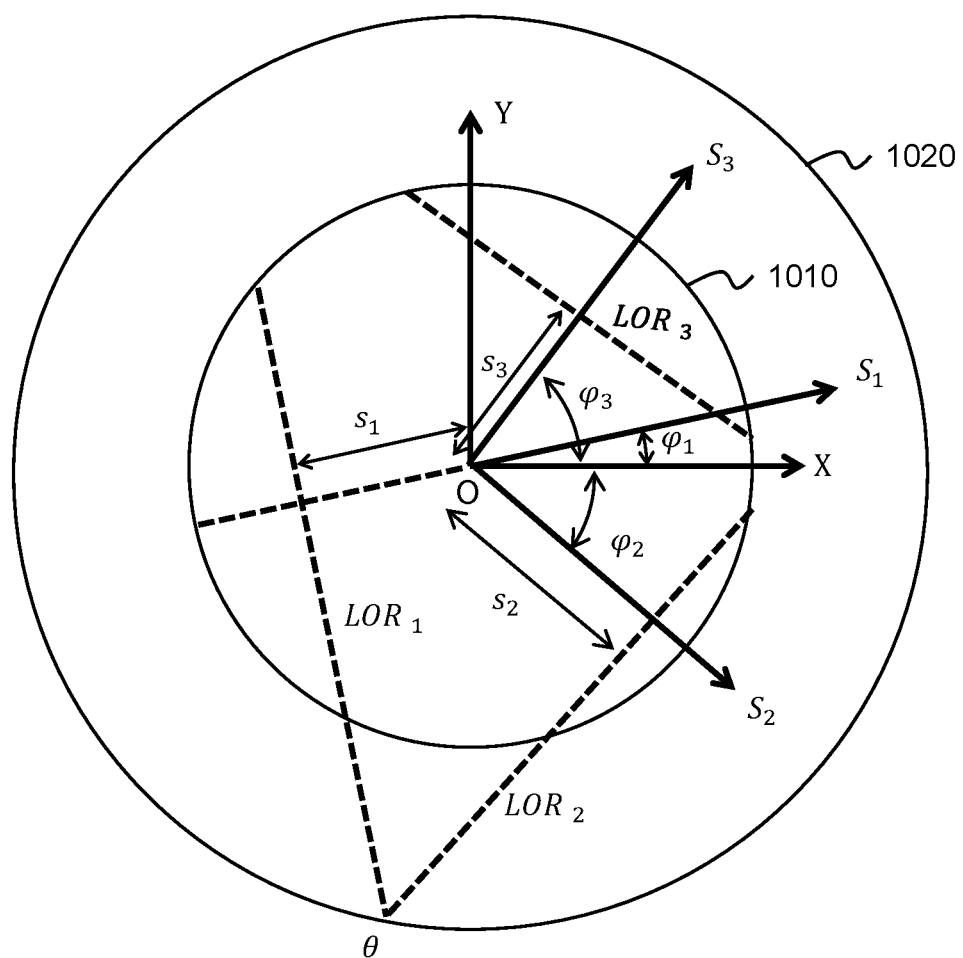
FIG. 10B is a schematic diagram illustrating exemplary LORs and corresponding h function values according to some embodiments of the present disclosure.

FIG. 10B is a schematic diagram illustrating exemplary LORs and corresponding h function values according to some embodiments of the present disclosure. As illustrated in FIG. 10B, an $LOR_1$ may be defined by a distance ($s_1$) of the $LOR_1$ from the center point O of the transverse scan field 1010, and an angle of orientation ($\varphi_1$) of the $LOR_1$ (i.e., the angle between $LOR_1$ and the vertical axis Y, and also the angle between the line $S_1$ that is vertical to the $LOR_1$ and the horizontal axis X). An $LOR_2$ may be defined by a distance ($s_2$) of the $LOR_2$ from the center point O of the transverse scan field 1010, and an angle of orientation ($\varphi_2$) of the $LOR_2$ (i.e., the angle between $LOR_2$ and the vertical axis Y, also the angle between the line $S_2$ that is vertical to the $LOR_2$ and the horizontal axis X). An $LOR_3$ may be defined by a distance ($s_3$) of the $LOR_3$ from the center point O of the transverse scan field 1010, and an angle of orientation ($\varphi_3$) of the $LOR_3$ (i.e., the angle between $LOR_3$ and the vertical axis Y, and also the angle between the line $S_3$ that is vertical to the $LOR_3$ and the horizontal axis X). The events occurred in the $LOR_1$ and $LOR_2$ may be detected by a detector unit located at angle $\theta$ of the detector ring 1020, while the events occurred in the $LOR_3$ may not be detected by the detector unit located at angle $\theta$. According to the h function, h(s, $\varphi$, $\theta$)=1 if and only if the LOR at (s, $\varphi$) is detected by the detector unit located at angle $\theta$. Otherwise, h(s, $\varphi$, $\theta$)=0. For the $LOR_1$, h($s_1$, $\varphi_1$, $\theta$)=1. For the $LOR_2$, h($s_2$, $\varphi_2$, $\theta$)=1. For the $LOR_3$, h($s_3$, $\varphi_3$, $\theta$)=0.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of a carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed subject matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and describe.

What is claimed is:

1. A system, comprising:
at least one storage medium including a set of instructions for reconstructing an activity map and an attenuation map to produce a positron emission tomography (PET) image; and
at least one processor configured to communicate with the at least one storage medium, wherein when executing the set of instructions, the system is directed to:
acquire, based on a PET system, a first dataset relating to coincidence events with time of flight (TOF) information, and a second dataset relating to single events or delay events, wherein both the single events and the delay events are correlated with random events;
determine, based on the first dataset, a plurality of data points associated with a boundary of a subject;
obtain an initial activity map and an initial attenuation map according to the boundary;
in each one of a plurality of iterations:
generate, based on the first dataset, an estimated activity map and an estimated attenuation map according to at least one image reconstruction algorithm;
determine an estimated second dataset based on the estimated activity map and the estimated attenuation map; and
update, based on the second dataset and the estimated second dataset, the estimated activity map and the estimated attenuation map to obtain an updated activity map and an updated attenuation map; and determine a target activity map and a target attenuation map.

2. The system of claim 1, wherein to generate an estimated activity map and an estimated attenuation map according to at least one image reconstruction algorithm, the system is further directed to:
generate, based on the initial activity map or updated activity map obtained in the (N−1)-th iteration, the estimated activity map using a first algorithm, wherein N is an integer that is greater than or equal to 2; and
generate, based on the initial attenuation map or updated attenuation map obtained in the (N−1)-th iteration, the estimated attenuation map using a second algorithm, wherein N is an integer that is greater than or equal to 2.

3. The system of claim 2, wherein the first algorithm is a maximum likelihood expectation maximization (MLEM) algorithm and the second algorithm is a maximum likelihood for transmission tomography (MLTR) algorithm.

4. The system of claim 1, wherein the system is further directed to:
obtain, based on the first dataset, a third dataset relating to coincidence events without TOF information; and
determine a plurality of pixel values corresponding to the image domain of the third dataset.

5. The system of claim 4, wherein to update the estimated activity map and the estimated attenuation map, the system is further directed to:
determine a first relationship associated with the estimated activity map, the second dataset, and the estimated second dataset; and determine a second relationship associated with the estimated attenuation map, the second dataset, the estimated second dataset, and the plurality of pixel values.

6. The system of claim 5, wherein to update the estimated activity map and the estimated attenuation map, the system is further directed to:
update the estimated activity map to obtain the updated activity map according to the first relationship; and
update the estimated attenuation map to obtain the updated attenuation map according to the second relationship.

7. The system of claim 5, wherein at least one of the first relationship and the second relationship includes a ratio of the second dataset to the estimated second dataset.

8. The system of claim 1, wherein the target activity map and the target attenuation map are determined when at least one of the estimated activity map, the estimated attenuation map, at least one of the updated activity map and the updated attenuation map is convergent, or an iteration count of the plurality of iterations exceeds a predetermined threshold.

9. The system of claim 1, wherein the system is further directed to:
generate, based on the target activity map and the target attenuation map, the PET image.

10. A method for reconstructing an activity map and an attenuation map to produce a positron emission tomography (PET) image, the method being implemented on at least one machine each of which has at least one processor and storage, the method comprising:
acquiring, based on a PET system, a first dataset relating to coincidence events with time of flight (TOF) information, and a second dataset relating to single events or delay events, wherein both the single events and the delay events are correlated with random events;
determine, based on the first dataset, a plurality of data points associated with a boundary of a subject;
determining an initial activity map and an initial attenuation map according to the boundary;
in each one of a plurality of iterations:
generating, based on the first dataset, an estimated activity map and an estimated attenuation map according to at least one image reconstruction algorithm;
determining an estimated second dataset based on the estimated activity map and the estimated attenuation map; and
updating, based on the second dataset and the estimated second dataset, the estimated activity map and the estimated attenuation map to obtain an updated activity map and an updated attenuation map; and
determining a target activity map and a target attenuation map.

11. The method of claim 10, wherein the generating an estimated activity map and an estimated attenuation map according to at least one image reconstruction algorithm further comprises:
generating, based on the initial activity map or updated activity map obtained in the (N−1)-th iteration, the estimated activity map using a first algorithm, wherein N is an integer that is greater than or equal to 2; and
generating, based on the initial attenuation map or updated attenuation map obtained in the (N−1)-th iteration, the estimated attenuation map using a second algorithm, wherein N is an integer that is greater than or equal to 2.

12. The method of claim 11, wherein the first algorithm is a maximum likelihood expectation maximization (MLEM) algorithm and the second algorithm is a maximum likelihood for transmission tomography (MLTR) algorithm.

13. The method of claim 10, wherein the updating the estimated activity map and the estimated attenuation map further comprises:
updating the estimated activity map to obtain the updated activity map according to a first relationship; and
updating the estimated attenuation map to obtain the updated attenuation map according to a second relationship.

14. The method of claim 13, wherein at least one of the first relationship and the second relationship includes a ratio of the second dataset to the estimated second dataset.

15. The method of claim 10, wherein the target activity map and the target attenuation map are determined when at least one of the estimated activity map, the estimated attenuation map, the updated activity map, and the updated attenuation map is convergent, or an iteration count of the plurality of iterations exceeds a predetermined threshold.

16. The method of claim 10, further comprising:
generating, based on the target activity map and the target attenuation map, the PET image.

17. The method of claim 14, wherein
the first relationship is associated with the estimated activity map, the second dataset, and the estimated second dataset, and
the second relationship is associated with the estimated attenuation map, the second dataset, the estimated second dataset, and a plurality of pixel values corresponding to a third dataset that relates to coincidence events without TOF information.

18. A method for processing, by a processor of a computer, positron emission tomography (PET) information obtained from a PET detector, the method comprising:
acquiring positron emission tomography (PET) data generated by scanning a subject;
acquiring scanned single events or scanned delay events based on the PET data, wherein both the single events and the delay events are correlated with random events;
obtaining a target activity map and a target attenuation map by performing operations including:
i) determining an initial activity map and an initial attenuation map based on a boundary image of the subject created using the PET data;
ii) iteratively reconstructing an estimated activity map and an estimated attenuation map based on the PET data;
iii) determining estimated single events or estimated delay events based on the estimated activity map and the estimated attenuation map;
iv) updating the estimated activity map and the estimated attenuation map based on the estimated single events and the scanned single events, or the estimated delay events and the scanned delay events to generate an updated activity map and an updated attenuation map;
v) repeating ii) through iv) until one or more termination criteria are satisfied.

19. The method of claim 18, wherein the termination criteria are that at least one of the estimated activity map, the estimated attenuation map, the updated activity map and the updated attenuation map is convergent, or an iteration count of the plurality of iterations exceeds a predetermined threshold.

20. The method of claim 18, further comprising:
generating, based on the target activity map and the target attenuation map, the PET image.

* * * * *